US009339273B2

(12) United States Patent
Weisshaupt et al.

(10) Patent No.: US 9,339,273 B2
(45) Date of Patent: May 17, 2016

(54) SURGICAL SYSTEM FOR CONNECTING BODILY TISSUE AND PROCESS FOR CUTTING PROTRUDING TISSUE

(75) Inventors: Dieter Weisshaupt, Immendingen (DE); Anton Keller, Duerbheim (DE); Christoph Rothweiler, Donaueschingen (DE)

(73) Assignee: Aesculap AG (DE)

( * ) Notice: Subject to any disclaimer, the term of this patent is extended or adjusted under 35 U.S.C. 154(b) by 429 days.

(21) Appl. No.: 13/516,090

(22) PCT Filed: Dec. 17, 2010

(86) PCT No.: PCT/EP2010/070017
§ 371 (c)(1),
(2), (4) Date: Aug. 27, 2012

(87) PCT Pub. No.: WO2011/083026
PCT Pub. Date: Jul. 14, 2011

(65) Prior Publication Data
US 2013/0035683 A1   Feb. 7, 2013

(30) Foreign Application Priority Data
Dec. 17, 2009   (DE) .......................... 10 2009 059 195

(51) Int. Cl.
*A61B 17/32*   (2006.01)
*A61B 17/11*   (2006.01)
(Continued)

(52) U.S. Cl.
CPC ......... *A61B 17/1114* (2013.01); *A61B 17/0643* (2013.01); *A61B 17/115* (2013.01);
(Continued)

(58) Field of Classification Search
CPC . A61B 17/32; A61B 17/3209; A61B 17/3093
USPC .......................................................... 607/45
See application file for complete search history.

(56) References Cited

U.S. PATENT DOCUMENTS

| 5,810,811 A | 9/1998 | Yates et al. |
|---|---|---|
| 6,270,497 B1 | 8/2001 | Sekino |

(Continued)

FOREIGN PATENT DOCUMENTS

| CN | 101528146 | 9/2009 |
|---|---|---|
| DE | 69420650 T2 | 9/1999 |

(Continued)

OTHER PUBLICATIONS

Examination Report issued in related Japanese Application No. 2012-543775, drafted on Jul. 26, 2013.
(Continued)

*Primary Examiner* — Joseph Dietrich
(74) *Attorney, Agent, or Firm* — RatnerPrestia

(57) ABSTRACT

The invention relates to improving a surgical system for bonding bodily tissue, comprising a surgical instrument having a bonding device for bonding bodily tissue, said bonding device comprising two tool elements displaceable relative to each other, wherein the instrument comprises a cutting device having a cutting element for cutting through tissue, and the cutting element is displaceably disposed relative to at least one of the tool elements, such that the cutting device is implemented in the form of an HF cutting device, wherein the cutting element comprises a cutting edge defining a cutting plane at an angle relative to a longitudinal axis defined by the instrument in the region of the bonding device.

20 Claims, 19 Drawing Sheets

(51) Int. Cl.
*A61B 17/064* (2006.01)
*A61B 17/115* (2006.01)
*A61B 17/3205* (2006.01)
*A61B 18/14* (2006.01)
*A61B 18/00* (2006.01)

(52) U.S. Cl.
CPC ....... *A61B18/1447* (2013.01); *A61B 17/32053* (2013.01); *A61B 18/1442* (2013.01); *A61B 2017/111* (2013.01); *A61B 2017/1132* (2013.01); *A61B 2018/0063* (2013.01); *A61B 2018/00601* (2013.01); *A61B 2018/00619* (2013.01); *A61B 2018/1412* (2013.01); *A61B 2018/1455* (2013.01); *A61B 2018/1467* (2013.01)

(56) References Cited

U.S. PATENT DOCUMENTS

| | | | |
|---|---|---|---|
| 6,395,002 | B1 | 5/2002 | Ellman et al. |
| 7,025,763 | B2 | 4/2006 | Karasawa |
| 7,168,604 | B2 | 1/2007 | Milliman |
| 7,608,073 | B2 | 10/2009 | Heinrich |
| 2003/0045811 | A1 | 3/2003 | Hinchliffe et al. |
| 2003/0069571 | A1 | 4/2003 | Treat et al. |
| 2004/0044356 | A1 | 3/2004 | Young et al. |
| 2006/0064086 | A1 | 3/2006 | Odom |
| 2008/0015566 | A1 | 1/2008 | Livneh |
| 2008/0210739 | A1 | 9/2008 | Milliman |
| 2008/0243121 | A1 | 10/2008 | Takashino et al. |
| 2009/0043305 | A1 | 2/2009 | Brodbeck et al. |
| 2011/0125176 | A1 | 5/2011 | Yates |

FOREIGN PATENT DOCUMENTS

| | | |
|---|---|---|
| DE | 69836817 T2 | 10/2007 |
| EP | 1 815 805 | 8/2007 |
| EP | 1 935 348 | 6/2008 |
| EP | 2 030 578 | 3/2009 |
| EP | 2 111 812 | 10/2009 |
| JP | 2008-018226 A | 1/2008 |
| JP | 2009-056306 A | 3/2009 |
| JP | 2009261907 | 11/2009 |
| SU | 1553089 A1 | 3/1990 |
| WO | WO 2005/004734 | 1/2005 |
| WO | WO 2006/021269 | 3/2006 |
| WO | WO 2009/022614 | 2/2009 |

OTHER PUBLICATIONS

Examination Report issued in related Canadian Application No. 2,784,110, mailed Sep. 13, 2013.
German Application Serial No. 102009059195.8, German Search Report mailed Oct. 5, 2010 (w/English ledger).
Russian Examination Report issued in related Russian Application No. 2012130088, issued Oct. 23, 2014.
Canadian Examination Report issued in related Canadian Application No. 2,784,111, dated May 2, 2014.
Entire patent prosecution history of U.S. Appl. No. 13/516,083, filed, Aug. 22, 2012, entitled, "Surgical System and Control Process for a Surgical Instrument and Process for Connecting Bodily Tissues."
International Search Report for International Application No. PCT/EP2010/070018 dated Mar. 18, 2011.
Chinese Search Report for Application No. 2010800609861 dated Dec. 17, 2010.
Chinese Office Action for Application No. 201080060986.1 dated Nov. 17, 2015, including English language translation.
International Search Report for International Application No. PCT/EP2010/070017 dated Nov. 24, 2011.

SURGICAL SYSTEM FOR CONNECTING BODILY TISSUE AND PROCESS FOR CUTTING PROTRUDING TISSUE

CROSS REFERENCE TO RELATED APPLICATIONS

This application is the national phase entry under 35 U.S.C. §371 of International Application No. PCT/EP2010/070017, filed Dec. 17, 2010, and claims the benefit of priority of German Application DE 10 2009 059 195.8, filed Dec. 17, 2009, the contents of both applications being incorporated by reference herein for all purposes.

FIELD OF THE INVENTION

The present invention pertains to a surgical system for connecting body tissue, comprising a surgical instrument with a connecting means for connecting body tissue, which connecting means comprises two tool elements movable in relation to one another, whereby the instrument comprises a cutting means with a cutting element for cutting tissue and the cutting element is arranged movable in relation to at least one of the tool elements.

Furthermore, the present invention pertains to a process for cutting protruding tissue from tubular body tissues connected previously to one another into a single tubular tissue.

BACKGROUND

Surgical instruments of surgical systems of the type described in the introduction are, for example, known in the form of coagulation instruments, in which protruding, coagulated tissue can be cut with a corresponding, provided cutting means. Furthermore, clip suture devices, with which tubular tissues can be connected to one another in a circular manner, for example, for creating end-to-end anastomoses, and precisely by applying clips, are known. Here, it is usual to equip the clip suture devices with ring knives, i.e., with knives, which have self-contained circular cutting edges.

The drawback in all prior-art surgical systems is that partly very high forces are needed for cutting the body tissue.

Therefore, the object of the present invention is to perfect a surgical system as well as a process of the type described in the introduction such that body tissue can be cut with lower cutting forces.

SUMMARY

This object is accomplished according to the present invention with a surgical system of the type described in the introduction in that the cutting element has a cutting edge, which defines a cutting plane sloped in relation to a longitudinal axis defined by the instrument in the area of the connection means.

A surface pressure between the cutting element and the tissue can especially be prevented by means of a cutting element with sloped cutting edge in relation to the longitudinal axis of the connection means. Rather, because of the slope, a selective introduction of force at the moment or point in time of the cutting is possible with such a cutting element. Thus, the forces, which are needed for cutting tissue, and especially at the moment of cutting, are markedly lower than in an extensive cutting. An extensive cutting is especially present when the cutting edge defines a cutting plane that runs at right angles to the longitudinal axis of the instrument in the area of the connection means. Due to the sloped cutting edge, the point of intersection may travel along the cutting edge especially also in circular cutting, and starting from a cutting area of the cutting edge, which has the shortest distance of the entire cutting edge from same especially before coming into contact with the tissue to be cut. Designing the cutting element in the manner described has advantages both in a purely mechanical use but also in a monopolar or bipolar embodiment. Especially in the case of a monopolar or bipolar cutting means, the only selective placement of the cutting edge on the tissue to be cut and the thus connected selective current concentration makes possible a problem-free cut and a homogeneous cutting pattern overall. Consequently, the energy needed for performing a cut is markedly reduced both in the mechanical and in the electrical cutting of body tissue.

The surgical system can be designed in an especially simple manner, when the cutting means is designed in the form of a mechanical cutting means. For example, the cutting edge can be designed in the form of a sharpened cutting edge. This can, for example, be designed by grinding a suitable, preferably hardened instrument steel.

Furthermore, it may be advantageous when the cutting means is designed in the form of an RF cutting means. An RF cutting means makes it possible to cut tissue by means of an RF current. A coagulation of same can be achieved with this especially during the cutting of the tissue, as a result of which undesired bleedings can be prevented. Optionally, the RF cutting means may be provided in combination with a mechanical cutting means as well.

An especially simple embodiment of a surgical system may be achieved, especially by providing an RF cutting means, by the cutting means being designed in the form of a monopolar cutting means.

An especially clean and defined cut can especially be carried out in a simple manner if the cutting means is designed in the form of a bipolar cutting means. This means that, for example, the cutting element forms an electrode and a corresponding counterelectrode is provided at the instrument, whereby the RF current flows between the electrode and the counterelectrode through the tissues to be connected.

Especially for cutting tubular tissues connected to one another, for example, after creating an end-to-end anastomosis, it is advantageous when the cutting edge has a self-contained circular design. Consequently, a, for example, circular or oval cut can be made by a surgeon depending on the need in a simple and reliable manner, and with a mechanical or RF or a combined mechanical/RF cutting means.

In order to be able to apply a cutting current, for example, an RF current to the cutting element, in a monopolar or bipolar mode, in a defined manner, it is advantageous when the instrument has at least one cutting terminal that is connected in an electrically conductive manner to the cutting means.

The at least one cutting terminal is preferably connected in an electrically conductive manner to the cutting element. It may, especially in a bipolar cutting means, also be connected to a corresponding counterelectrode provided at the instrument. It is especially advantageous when two corresponding cutting terminals are provided.

In order to be able to connect tissue to one another in a simple manner with the surgical system, it is advantageous when the tool elements comprise an electrode each, which define a minimal distance from one another, lie opposite one another and point towards one another in a position of proximity of the tool elements. By means of corresponding feed of current to the electrodes, for example, two tissues to be connected to one another can be connected, which can be designated as welding or as sealing, in a simple manner. Here, it is especially desirable when a destruction of the cells involved does not occur.

Advantageously, at least one of the electrodes is designed as an RF electrode. This makes it possible to apply an RF current to one or both electrodes, which is especially suitable for connecting tissues, especially body tissues of a patient.

According to another preferred embodiment of the present invention, provisions may be made for at least one of the electrodes to be divided into at least two electrode segments, and for the at least two electrode segments to be electrically insulated from each other. The division of at least one of the RF electrodes into two or more electrode segments has especially the advantage that the process parameters for connecting tissues to be connected to one another can be controlled significantly more easily than in non-divided electrodes. The smaller the surfaces, between which the RF current is applied, the more easily the process parameters can be controlled. The temperature, pressure as well as tissue impedance especially have a considerable effect on the connection result. For example, it is thus also possible to adjust the process parameters optimally to the tissue quality and especially also automatically. Moreover, other than when using a clip suture device, no clips that would remain behind as foreign bodies in the body are needed. The electrode segments dividing the RF electrode or RF electrodes especially make a segmented feed of current to the RF electrode possible, such that the tissues to be connected to one another can be welded or sealed to one another in segments. A sequential current feed possible due to segmenting of the RF electrodes makes it possible, during the connection or sealing process, to introduce less energy into the tissues than in comparable, unsegmented RF electrodes. Further, the segmenting has the advantage that between areas connected by RF current feed of the tissues to be connected to one another, tissue areas remain unchanged and essentially undamaged, such that new cell growth starting from same is made possible, which, in addition to the connection brought about by the RF current, makes possible a permanent connection of the tissues by a growing together of same.

Furthermore, it may be advantageous when the cutting element is designed as rotatable about the longitudinal axis. Thus, with a predetermined position of the instrument, a position of the cut with the cutting element can be selected in an optional and desired manner.

To be able to improve the controllability of the process parameters even further, it is advantageous when each of the RF electrodes is divided into at least two electrode segments, which are electrically insulated from each other. In the sense of this application, at least two electrode segments means two or more electrode segments, i.e., especially three, four, five, six, seven, eight, nine, ten, eleven or twelve. However, more are also conceivable, and depending on the size of the tool elements 20, 25, 30 or 40 electrode segments as well.

Advantageously, at least one of the RF electrodes is divided into a plurality of electrode segments. In the sense of this application, a plurality of electrode segments is defined as two electrode segments, which make possible an even further improved controllability of the process parameters.

To be able to feed a current to the electrode segments specifically in a simple and reliable manner, it is advantageous when each electrode segment is connected in an electrically conductive manner to a terminal contact.

It is advantageous when the tool elements have a tool element surface each and when at least one tool element surface is flat. This design makes it possible to design the tool elements practically without projections.

The tool element surface preferably has a circular design. Thus, circular connections, for example, in end-to-end anastomoses of tubular tissues, can be produced in a simple manner. The interaction with a cutting element, having a self-contained circular cutting edge, is thus especially also simple to embody.

It is advantageous if at least one of the electrodes has a self-contained circular design. Of course, all electrodes of the instrument may have a self-contained circular design. Tissue can thus be connected to one another in a simple and reliable manner in a circular pattern, which is advantageous for end-to-end anastomoses, in particular.

To be able to grip and optionally to hold tissue between the two tool elements during the connection process, it is advantageous when the tool elements are pivotable and/or displaceable in relation to one another. All in all, a movable arrangement of the tool elements in relation to one another is thus desirable. A pivotability or displaceability of the tool elements in relation to one another may also especially have advantages in the removal of the instrument. For example, a cross section of the instrument in the area of one or both tool elements for removing the instrument can thus be reduced.

According to another preferred embodiment, provisions may be made for the instrument to have a shaft, at the distal end of which at least one of the tool elements is arranged or formed. In this way, the instrument may have an especially compact design. Further, the stability of the instrument can be increased overall due to the arrangement or formation of at least one of the tool elements at the distal end of the shaft. Thus, it is especially also possible to design one of the tool elements in a simple manner as fixed in relation to the shaft.

It is advantageous when a first tool element comprises an edge surface of the shaft pointing in the distal direction or essentially in the distal direction. For example, a distal end of the shaft can thus be pressed or held against a tissue which will be connected to another tissue in a simple manner. Moreover, a defined tool element surface may thus also be predetermined in a simple and reliable manner.

In another preferred embodiment, provisions may also be made for a second tool element to comprise an electrode element that is movable in the shaft direction and movable in the direction of the first tool element and away from same. This embodiment makes it possible, for example, to move the two tool elements in relation to one another such that tissues to be connected to one another can be held in a defined manner between them and can be connected to one another by means of corresponding application of RF current.

So that the tool elements can be moved in relation to one another in a simple manner, it is advantageous when the instrument comprises an actuation means for moving the tool elements in relation to one another.

It is advantageous when the instrument comprises a cutting actuation means for moving the cutting element and at least one of the tool elements in relation to one another. This enables a surgeon to connect tissues to one another first with the instrument and then to cut the tissues with the cutting means, selectively directly subsequently or even at a later point in time. It is also especially conceivable to couple the cutting actuation means with the actuation means, for example, such that at the end of the connection process, protruding tissues are automatically cut with the cutting means.

To further improve the manageability of the surgical instrument, the actuation means and/or cutting actuation means are arranged or formed at a proximal end of the instrument. For example, when the instrument has a shaft, this can be inserted through a body opening into the interior of the patient's body, whereby the tool elements can then be actuated in relation to one another and/or in relation to the cutting means by means of the actuation means or the cutting actuation means, which preferably still protrude from the body of the patient. Overall, an endoscopic or minimally invasive instrument can thus be designed in a simple manner.

The manageability of the instrument can especially be improved for a surgeon in that the actuation means and/or the cutting actuation means comprises two actuation members, which are pivotable in relation to one another, which are in operative connection with at least one of the tool elements or the cutting element for transmitting an actuation force for moving the at least one tool element in relation to the other tool element or the at least one tool element in relation to the cutting element. The actuation members may also basically be designed as only movable in relation to one another, i.e., as an alternative, for example, to a pivotable arrangement they may be arranged displaceable, or pivotable and displaceable, to one another as well To be able to apply an RF current to the RF instrument in a desired manner, the surgical system preferably comprises at least one RF current generator, which can be selectively connected in an electrically conductive manner to the RF electrodes and/or to the cutting element. The optimal current for the connection or cutting of tissue, respectively, can thus especially be adjusted.

The object stated in the introduction is further accomplished according to the present invention with a process for cutting protruding tissue from tubular body tissues which were connected previously to one another into a single tubular tissue, in that the two connected body tissues are held and in that the body tissues, starting from a point circulating about a longitudinal axis defined by the single tubular tissue, are cut.

Due to the suggested process, markedly lower cutting forces are needed than is the case in knives, whose cutting edges impact simultaneously with all points on the tissue to be separated. Thus, a cleaner cut starting from the point mentioned, which may also be designated as the starting point, can thus be made possible, and both with mechanical and with mono- or bipolar electrical cutting means.

In order to be able to remove protruding tissue in end-to-end anastomoses in a defined manner, it is advantageous when a circular cutting element is used.

Advantageously, a current is applied to the cutting element for cutting. It may especially be an RF current. Optionally, the tissue may be cut both mechanically and electrosurgically, whereby the electrosurgical procedure has the advantage that possible bleedings occurring during the cutting of the tissue can be stopped by means of instantaneous coagulation.

BRIEF DESCRIPTION OF THE DRAWING FIGURES

The following description of preferred embodiments of the present invention is used for a detailed explanation in connection with the drawings. In the drawings, FIG. 1 shows a schematic general view of a surgical instrument for connecting body tissues;

DETAILED DESCRIPTION

Figure 1:
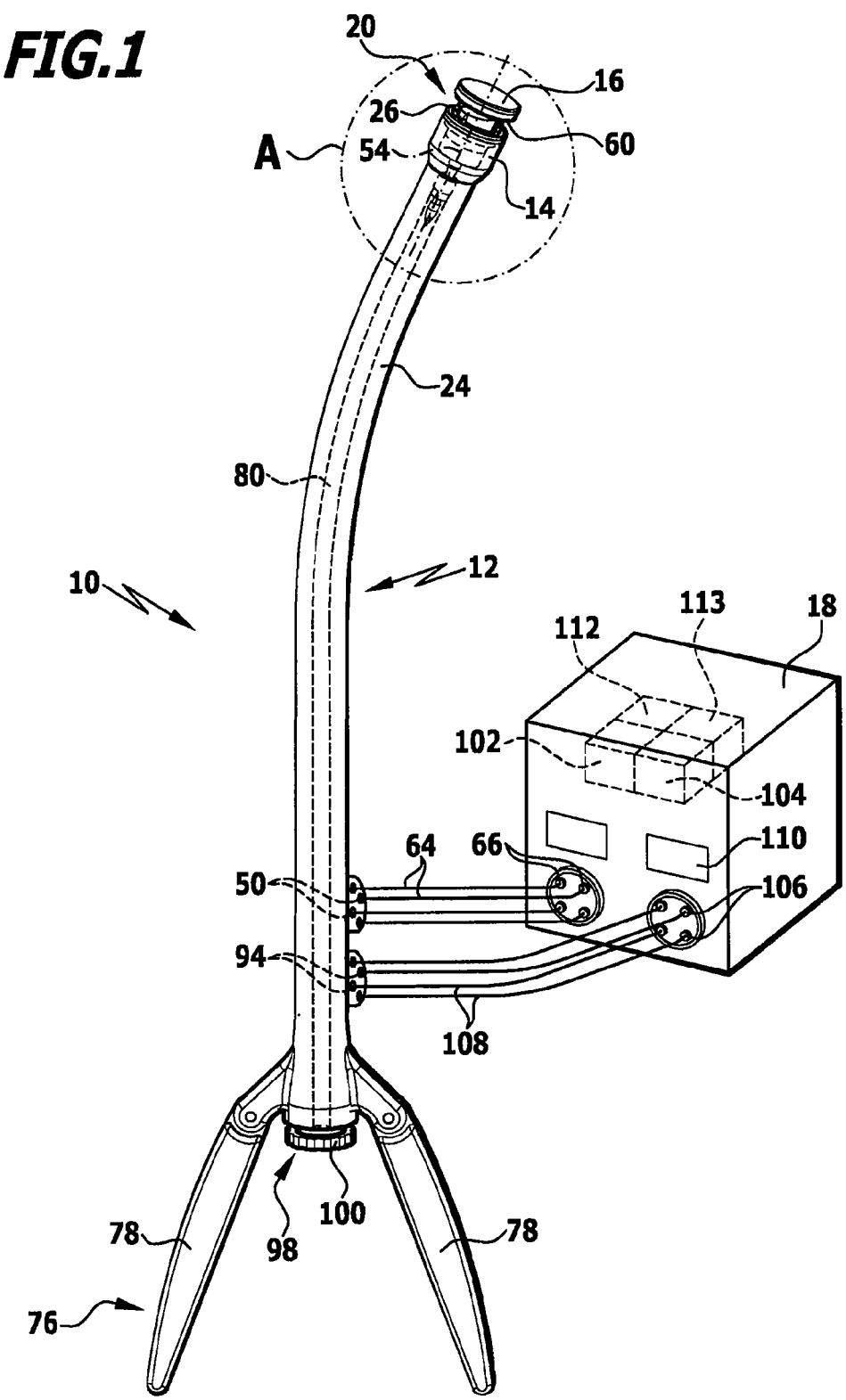

A surgical system for connecting body tissue is schematically shown in FIG. 1 and is designated as a whole with reference number 10. It comprises a surgical instrument 12 with two tool elements 14 and 16 which are movable in relation to one another. Further, the system 10 comprises a current generator in the form of an RF current generator 18, which can be connected to the instrument 12 in another manner described in detail below.

The tool elements 14 and 16 form a part of a connecting means, provided as a whole with reference number 20, for connecting body tissue. The first tool element 14 comprises an edge surface 22, pointing in the distal direction, of an elongated, sleeve-like shaft 24 of the instrument 12. Thus, the first tool element is arranged or formed at a distal end 26 of the instrument 12.

The first tool element 14 comprises an RF electrode 28. It is divided into at least two electrode segments 30, into four electrode segments 30 in the exemplary embodiment schematically shown in FIGS. 2 through 5, which are electrically insulated from each other. The electrode segments 30 are designed as strip-shaped or essentially strip-shaped. The first tool element 14 defines a tool element surface 32 such that the RF electrode 28 forms a part of same. All in all, the tool element surface 32 is designed as flat and circular.

The four electrode segments 30 define two rows of electrodes 34 and 36. Each row of electrodes comprises a part of the four electrode segments 30 each. As can be seen, for example, in FIG. 5, each electrode segment 30 has a first electrode segment section 38, which forms a part of the first row of electrodes 34, and a second electrode segment section 40, which forms a part of the second row of electrodes 36. The two rows of electrodes 34 and 36 have an overall curved design, whereby the electrode segment sections 38 and 40 define electrically conductive circular ring sections each. All in all, the at least two rows of electrodes, which are defined by four electrode segment sections 38 or 40 each, have a self-contained circular design. To be able to contact the electrode segments 30 in a desired manner, each electrode segment 30 is connected in an electrically conductive manner to a terminal contact 42 which is arranged in a connection area between the electrode segment sections 38, 40. Even after tissues are connected by RF current feed, completely or essentially undamaged cells, from which new cell growth can start, remain behind between the rows of electrodes. In the long term, this makes possible in addition to connecting tissues by welding a permanent connection of the tissues due to the growing together of intact cells.

RF electrode 28 defines an electrode center line 44 running between the electrode segment sections 38 and 40. Therefore, electrode segments 30 which are adjacent to one another are arranged offset to one another in a direction defined by the electrode center line 44. All in all, the RF electrode 28 divided into four electrode segments 30 defines an electrode length 46, whereby each of the four electrode segments 30 defines a segment length 48 that is shorter than the electrode length 46. As shown, for example, in FIG. 5, electrode segments 30 extend over an angle range of approx. 140° and thus have a length that corresponds to approximately 40% of the electrode length 46. Thus, the sum of all segment lengths 48 is, however, also approx. greater by a factor of 1.6 than the electrode length 46.

RF terminal contacts 50, which are connected in an electrically conductive manner, for example, via lines running in the shaft, to the electrode segments 30, are arranged in the area of a proximal end of the shaft 24. The number of RF terminal contacts 50 preferably corresponds to the number of electrode segments 30, i.e., four RF terminal contacts 50 for the four electrode segments 30 of the first tool element 14.

The second tool element 16 is designed as essentially disk-like and comprises an electrode element 52, which can be moved in the direction of the first tool element 14 and away from same as well as parallel to a longitudinal axis 54 of the shaft 24 in the area of the tool elements 14, 16 which defines a shaft direction 56. The tool elements 14, 16 are arranged displaceable in relation to one another, i.e., a distance 58 between the tool element surface 32 of the first tool element 14 and a tool element surface 60 of the second tool element 16 is variable.

The electrode element 52 comprises an RF electrode 29, which corresponds to the RF electrode 28 in its design. This means that it also comprises four electrode segments 31, which do not protrude over the tool element surface 60. Two rows of electrodes 35 and 37 are likewise defined, whereby first electrode segment sections 39 define the row of electrodes 35 and second electrode segment sections 41 define the row of electrodes 37. Terminal contacts 43 are likewise provided, which conductively connect an electrode segment section 39 to an electrode segment section 41 each for forming an electrode segment 31. RF electrodes 28 and 29 are designed as mirror-symmetrical to a mirror plane running at right angles to the longitudinal axis 54 between the tool element surfaces 32 and 60. In this way, pairs of electrode segments 62 are defined by an electrode segment 30 each and the corresponding electrode segment 31 lying opposite same. All in all, the exemplary embodiment shown in FIGS. 1 through 5 thus comprises four pairs of electrode segments 62. The electrode segments 30, 31 are not only geometrically similar, but also have the same size or essentially the same size.

Figure 4:
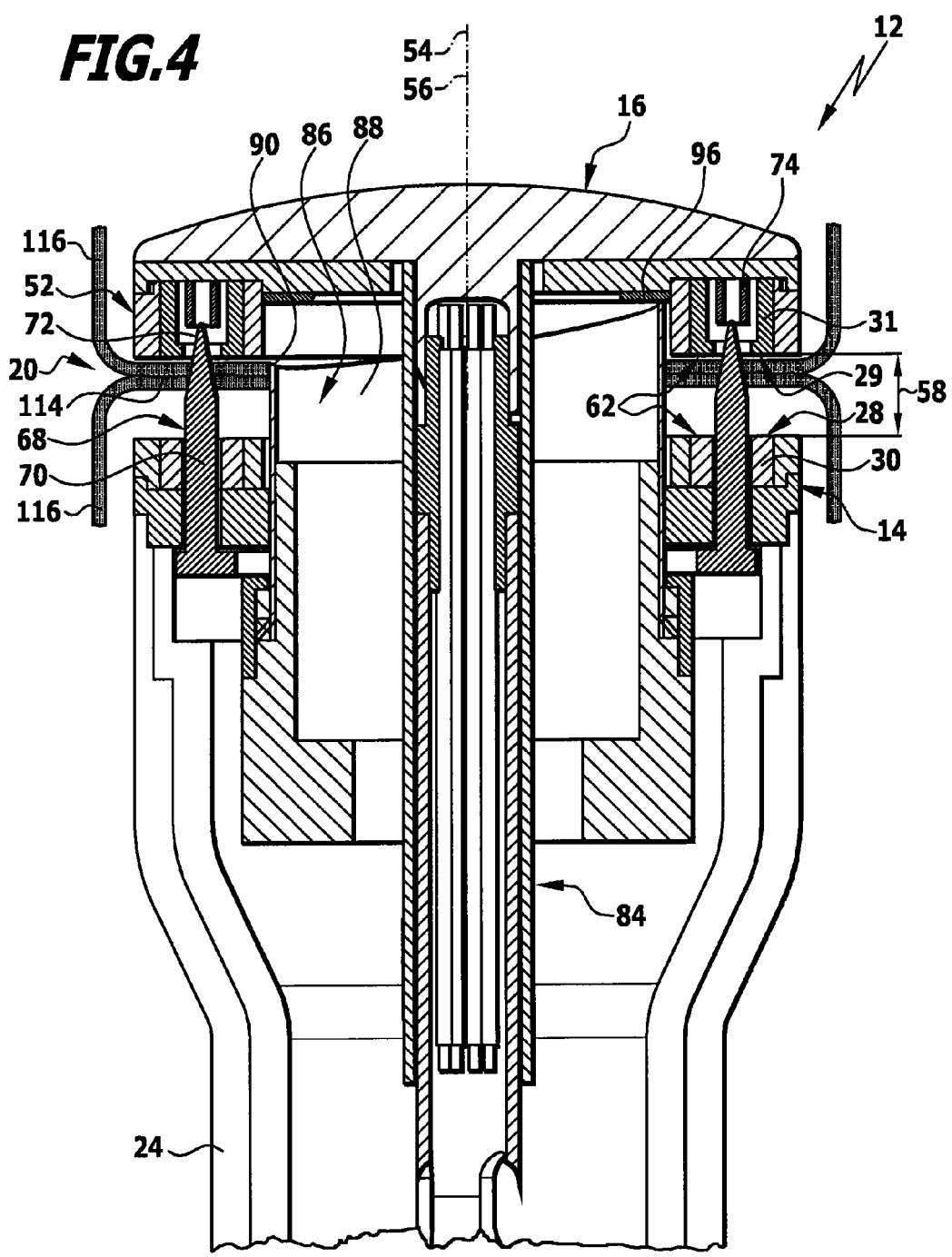
FIG. 4 shows a view similar to FIG. 3 when welding the tissues for creating an end-to-end anastomosis.
Figure 5:
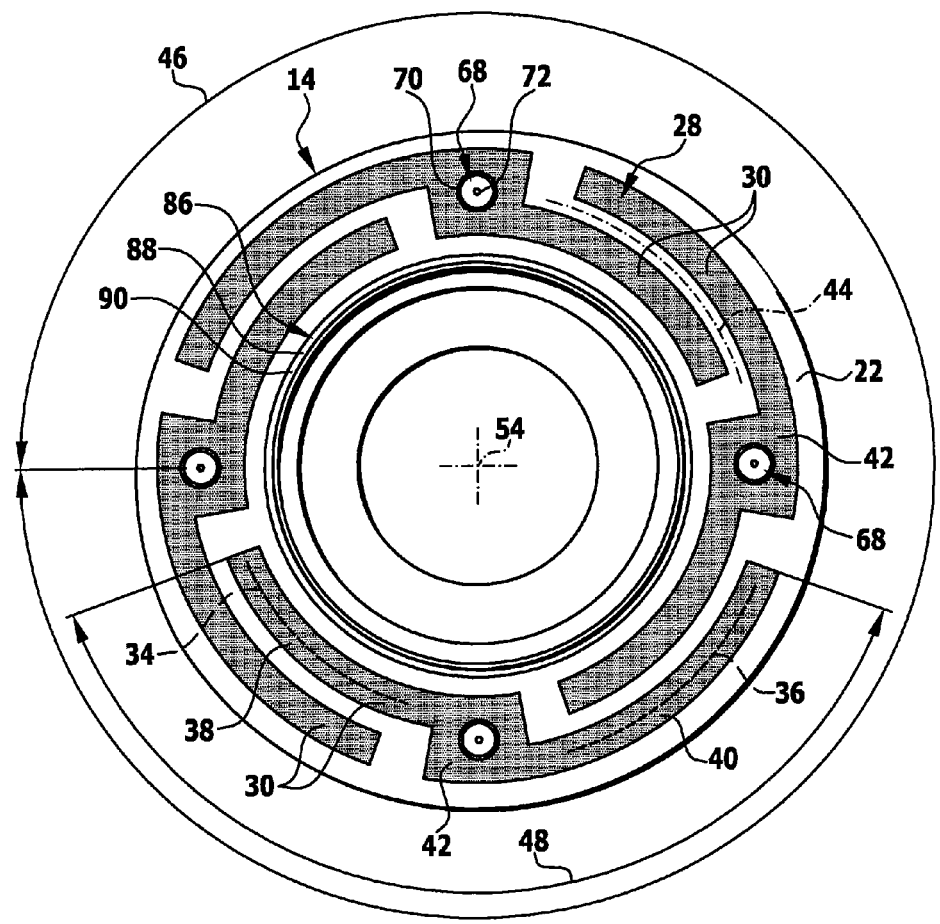
FIG. 5 shows a top view of a tool element surface with an RF electrode divided into four electrode segments.

The RF electrodes 28, 29 define a minimal distance 58 from one another in a position of proximity of the tool elements 14, 16. The position of proximity is schematically shown in FIG. 4. In the position of proximity, the RF electrodes 28 and 29 lie opposite one another and point towards one another.

The electrode segments 31 can be connected in an electrically conductive manner to another four RF terminal contacts 50, of which only two are shown in FIG. 1 for the sake of clarity. The RF terminal contacts 50 may be connected to corresponding contacts 66 of the RF current generator 18 by means of corresponding connecting lines 64. As already explained, the RF terminal contacts 50 are directly connected in an electrically conductive manner to the electrode segments 30. To be able to connect the RF terminal contacts 50 to the electrode segments 31, contact members 68, which have a short cylindrical section 70 and a cone-shaped section 72 defining a free end, are arranged projecting at the shaft 24 or at the first tool element 14 pointing in the direction of the second tool element 16. In a tissue connection position, as it is schematically shown, for example, in FIG. 4, i.e., in a position, in which tool elements 14 and 16 are located in the position of proximity, the free ends of the sections 72 of the contact members 68 extend into corresponding sleeve-like mounts 74 of the electrode element 52 and are in electrically conductive contact with same. Contact members 68 are in turn connected to the RF terminal contacts 50 along the shaft 24 via electrical lines (not shown). The mounts 74 are in turn connected in an electrically conductive manner to the terminal contacts 43. In this way, an electrically conductive contact between the RF terminal contacts 50 and the electrode segments 31 can also be made in the proximity position or tissue connection position.

Of course, contact members 68, which pass through the electrode segments 30 in the area of their terminal contacts 42, are insulated from same, so that no short-circuits can occur. For this purpose, the sections 70 of the contact members 68 are preferably provided with an electrically conductive coating or shell.

In order to be able to move the tool elements 14, 16 of the instrument 12 in relation to one another, an actuating means 76 is arranged at a proximal end or end area of the instrument 12. The actuating means 76 comprises two actuating members 78, which are pivotable in relation to one another and which are movably coupled with a force transmission member 80 mounted movably in the interior of the shaft, such that as a result of the pivoting movement of the actuating members 78, this is movable in the distal or proximal direction.

Figure 2:
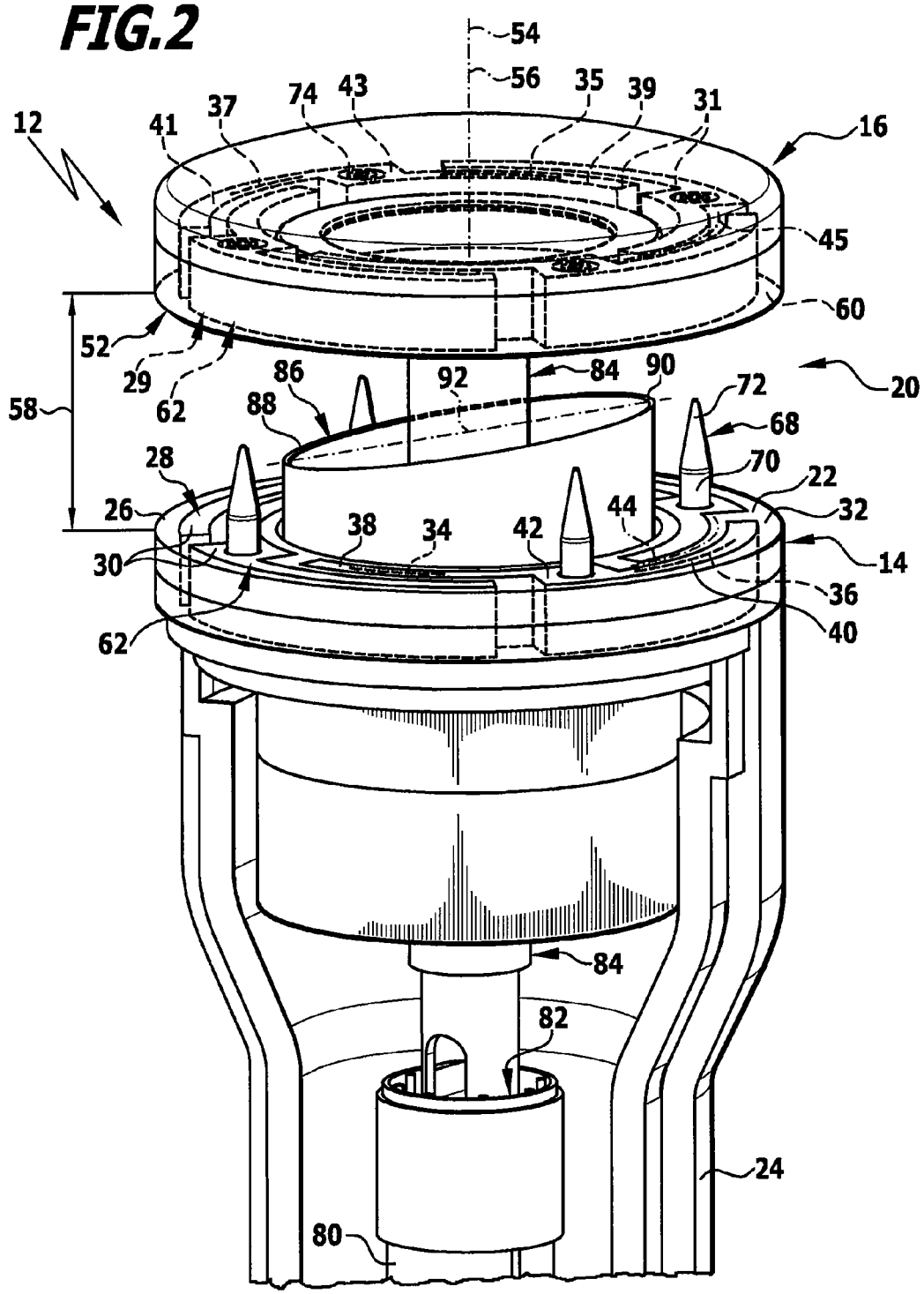
FIG. 2 shows an enlarged, perspective, partly sectional and open view of area A in FIG. 1.
Figure 3:
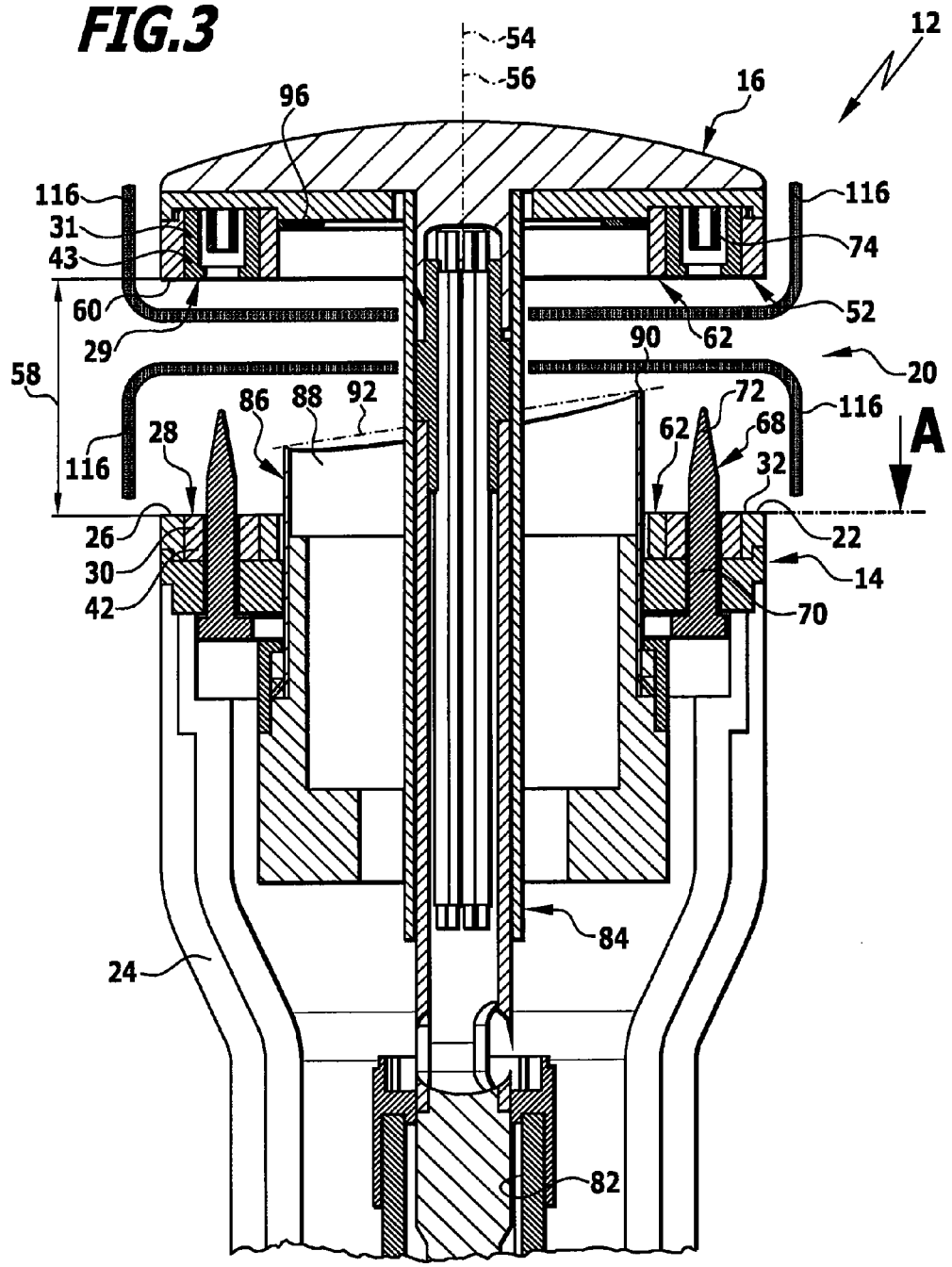
FIG. 3 shows a longitudinal sectional view of the instrument from FIG. 1 in area A before connecting two tubular tissues.

At its distal end, the force transmission member 80 defines a blind-hole-like mount 82, into which a holding member 84 with a first free end can be inserted and can then be fixed in the mount 82. The second free end of the essentially rod-shaped holding member 84 is immovably connected to the second tool element 16. In this way, as a result of a displacement of the force transmission member 80 in the distal direction, the second tool element 16 can be moved away from the first tool element 14. The instrument 12 is preferably designed, such that the second tool element 16 can be brought from a tissue gripping position, as it is schematically shown in FIGS. 2 and 3 and in which the tool elements 14, 16 have a maximum distance 58 from one another, into the position of proximity or the tissue connection position by pivoting the actuating members 78 towards one another, which results in a movement of the force transmission member 80 in the proximal direction.

Furthermore, the instrument comprises a cutting means 86 for cutting tissue. The cutting means 86 comprises a cutting element 88 with a self-contained circular cutting edge 90. The cutting edge 90 defines a cutting plane 92 sloped in relation to the longitudinal axis 54 of the instrument 12. The cutting plane 92 is sloped by approx. 10° in relation to a reference plane running at right angles to the longitudinal axis 54, which runs parallel to the tool element surfaces 32 and 33. On the proximal side, another RF cutting terminal 94, which in a variant of the instrument 12 is connected in an electrically conductive manner to the cutting element 88, is provided at the shaft 24. Thus, for example, a monopolar cutting means 86 can be implemented, whereby a neutral electrode would usually be applied for monopolar cutting at the body of the patient. A bipolar cutting means 86 is, for example, implemented by a ring electrode 96 being arranged opposite cutting edge 90 at the second tool element 16, which is connected to another RF cutting terminal 94 via an electrically conductive connection (which is not shown in detail), which runs, for example, through the force transmission member 80 in a manner not shown. The ring electrode 96 itself may also be selectively segmented, for example, similar to the RF electrodes 28 and 29. It would also be possible to use the RF electrode 29 as a counterelectrode instead of the ring electrode 96.

The cutting element 88 is preferably mounted displaceably in relation to the two tool elements 14, 16. The cutting edge 90, which is designed as concentric about the longitudinal axis 54, can thus be displaced in relation to the RF electrodes 28 and 29. For actuating the cutting means 86, a cutting actuating means 98 is provided with an actuating member 100 projecting from the proximal end of the instrument. This is mechanically coupled to the cutting element 88 via a mechanism (which is not shown), for example, another force transmission member running in the interior of the shaft 24, such that, as a result of a movement of the actuating member 100, the cutting element 88 is moved as well. The actuating member 100 is preferably arranged displaceably and rotatably in relation to the shaft 24, such that the cutting element 88 can be not only displaced parallel to the longitudinal axis 54, but also rotated in relation to same.

In order to be able to apply RF current to the electrode segments 30, 31 as desired, a control and/or regulating means 102 is provided with a switching means 104. The control and/or regulating means 102 is preferably arranged in a housing of the RF current generator and forms a part of same. The switching means 104 is especially designed for the sequential application of an RF current to the electrode segments 30, 31. The switching means 104 is especially used for controlling the contacts 66 as well as further contacts 106, which can be connected to the RF cutting terminals 94 of the instrument 12 via further connecting lines 108. In this way, the cutting means 86 can be operated in a monopolar or bipolar manner with the RF current generator 18. For the monopolar operation, RF current is applied only to the cutting element 88 and a neutral electrode is arranged at the body of the patient as a counterelectrode. For bipolar cutting, especially a circular counterelectrode may be provided at the second tool element 16, for example, in the form of the ring electrode 96, such that an RF current can then flow between the counterelectrode and cutting element 88. As an alternative, the RF electrode 29 may also be used as a counterelectrode. If a current feed of the cutting means 86 is entirely dispensed with, then this may also be used purely mechanically for cutting tissue and by means of the preferably sharpened cutting edge 90.

The switching means 104 may further also be designed such that RF current can be simultaneously applied to at least two electrode segments 30, 31 of an RF electrode 28, 29. It is advantageous here when another electrode segment 30, 31, which is then currentless, however, is arranged between two electrode segments 30, 31, to which RF current is applied simultaneously. For example, in this way the electrode segments 30 of the RF electrode 28 shown in FIG. 5 lying opposite one another might be fed current simultaneously, whereby the two other electrode segments 30 then remain currentless.

In order to be able to individually adjust a current feed intensity and/or a duration of current feed for the individual electrode segments 30, 31, the control and/or regulating means 102 is designed as comprising an adjusting means 110. By means of the adjusting means 110, for example, an intensity and/or a frequency of the RF current, just as a duration of current feed, can be adjusted. Moreover, the adjusting means 110 may optionally also be designed to be able to adjust current feed sequences individually.

Furthermore, the control and/or regulating means 102 preferably comprises a temperature measuring means 112 for measuring an electrode segment temperature and/or tissue temperature. Temperature measuring means 112 is especially used for supplying the control and/or regulating means 102 the controlled variables needed for an automatic regulation of a current feed of the RF electrodes 28, 29, especially a temperature of the tissue, for example, indirectly via a temperature measurement of the electrode segments 30, 31. For example, electrode segments 30, 31, which are not fed current, may be used as measuring contacts for determining the temperature via a measurement of the tissue impedance. In this way, it can be guaranteed that the temperature needed for connecting the tissue in a desired and highly precise manner is achieved by the corresponding feed of current to the RF electrodes 28, 29, but an undesired overheating of the tissues to be connected to one another is prevented.

Further, the control and/or regulating means 102 optionally comprises an impedance measuring means 113 for measuring a tissue impedance of tissue held between the tool elements 14 and 16. The determination of the tissue impedance makes it possible, depending on its value, to regulate the RF generator 18, especially the parameters of voltage, current or power provided by same. In this way, the energy to be introduced into same for connecting the tissues can be regulated in a simple and reliable manner. Especially the RF electrodes 28 and 29 can be used for measuring the tissue impedance. A measurement may also be performed between individual electrode segments 30 and 31, which lie opposite one another. The tissue impedance measurement may take place selectively during the current feed of RF electrodes 28, 29 or when RF electrodes 28, 29 are just currentless. Thus, the change in the tissues can be monitored well and practically in real time and further energy input can be metered, stopped or specifically further permitted.

With the surgical system 10 described above, especially tubular tissues 116 can be connected to one another directly by being welded or sealed to one another by means of RF current. In particular, the procedure is, for example, as follows:

For making an end-to-end anastomosis of two tubular tissues 116, as is necessary, for example, after a bowel surgery, in which a piece of the bowel is removed, free ends of the tissues 116 are brought towards one another, such that they lie against one another in a circular, flat manner, as shown, for example, in FIGS. 3 and 4, with their free ends pointing in the direction of the longitudinal axis. The free ends are then located between the two tool elements 14, 16, such that the tissues 116 can be held together, being gripped between the tool elements 14, 16 in the tissue gripping position.

The tool elements 14, 16 are then moved towards one another into the tissue connection position, such that the electrode segments 31 are also connected in an electrically conductive manner to the RF terminal contacts 50 in the manner described above. For welding the tissues 116, an RF current is now preferably applied to individual pairs of electrode segments 62, which then flows over the tissue sections held between the tool elements 14, 16 and heats same. At a temperature of approx. 50° C. to approx. 80° C., and preferably approx. 65° C. to approx. 70° C., a change takes places in the cells, such that the tissues 116 bond to one another. The connection process is preferably carried out such that always only one pair of electrode segments 62 is simultaneously fed current, especially in a sequential succession. In this way, a circular connecting line 114 is produced, which is essentially predetermined by the RF electrodes 28, 29 or their electrode center lines 44, 45.

The temperature can be much better controlled for connecting the tissues 116 and a destruction of the cells can be prevented by an RF current not being applied to all the RF electrodes 28, 29. The electrode segments 30, 31 are preferably fed current one after the other, i.e., sequentially, such that the tissues 116 are welded to one another in sections along the connecting line 114. Furthermore, a double connection between the tissues 116 is produced by the two-row arrangement of the electrode segment sections 38, 39, 40 and 41, which can guarantee an optimal sealing and a permanent, stable connection of the tissues 116 to one another.

As an alternative to a sequential current feed, as already indicated above, electrode segments 30, 31 lying opposite one another may also be fed current simultaneously, as a result of which the time for connecting the tissues 116 can be cut in half in the exemplary embodiment schematically shown in FIGS. 1 through 5.

After connecting the tissues 116, protruding tissue is removed by means of the cutting means 86. In this case, the cutting means 86 is preferably used in a bipolar mode, i.e., the cutting element 88 and the ring electrode 96 are connected to the RF current generator 18 and an RF current is conducted over the two tissues 116 to cut the tissue. Due to the sloped cutting edge 90, a defined cutting spark is produced, and precisely in the area in which the distance between the cutting edge 88 and the ring electrode 96 is minimal. Starting from this area, the cutting spark then travels automatically along the cutting edge 90 in both directions around in a circle until the tissue is completely severed. The use of the cutting means 86 in the bipolar mode of operation has especially the advantage that the tissues 116 are also simultaneously coagulated during the cutting in order to stop undesired bleeding directly during the cutting.

After connecting and cutting the tissues 116, the instrument 12 can then be withdrawn from the body of the patient, for example, from his/her bowel, by withdrawing the shaft 24.

Depending on the embodiment of the instrument 12, the shaft 24 is preferably so long that both the actuating means 76 and the cutting actuating means 98 still protrude from the body of the patient during the use of the instrument 12, so that they can be actuated by a surgeon.

Figure 6:
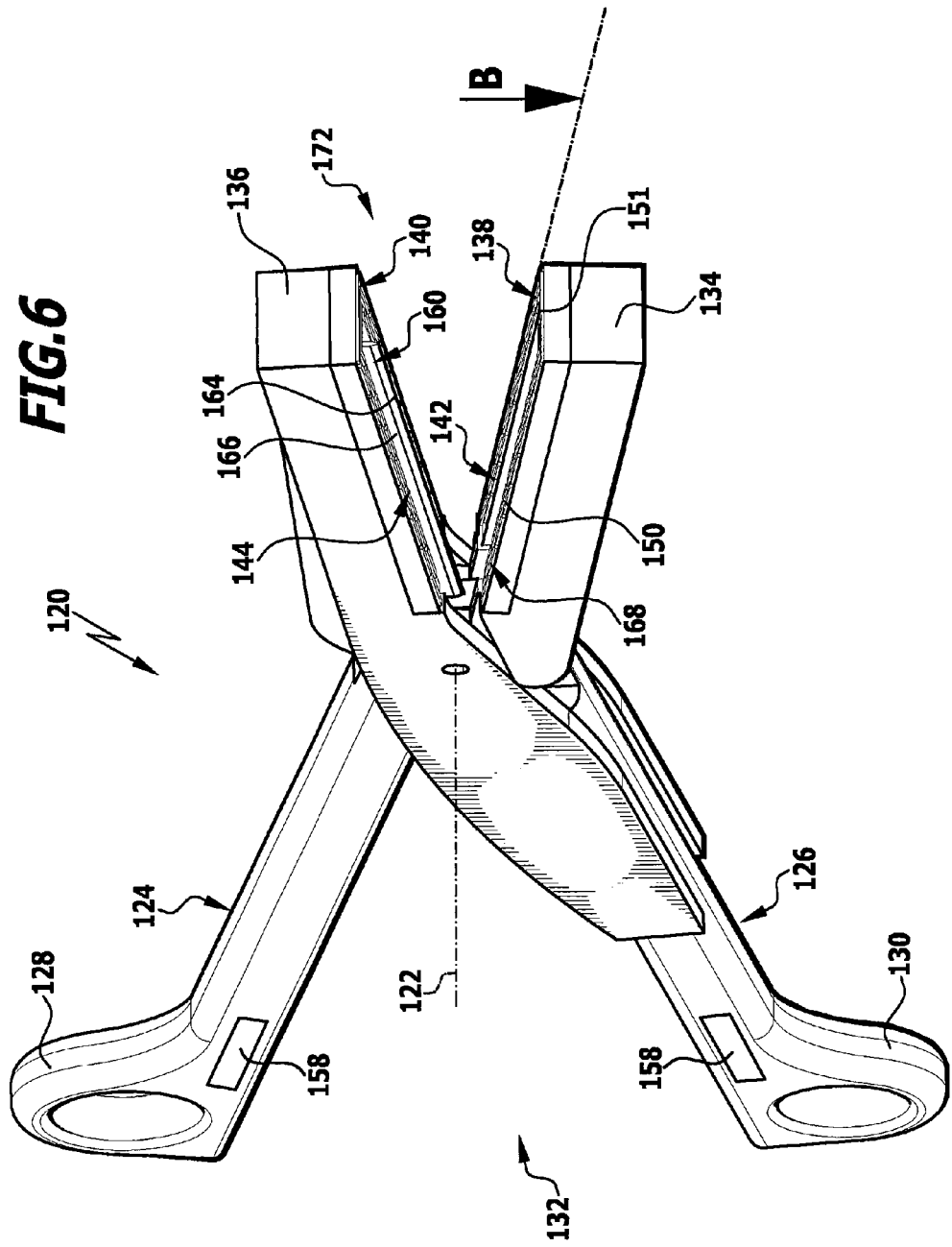
FIG. 6 shows a perspective, schematic view of a second exemplary embodiment of a surgical instrument for connecting body tissues.
Figure 7:
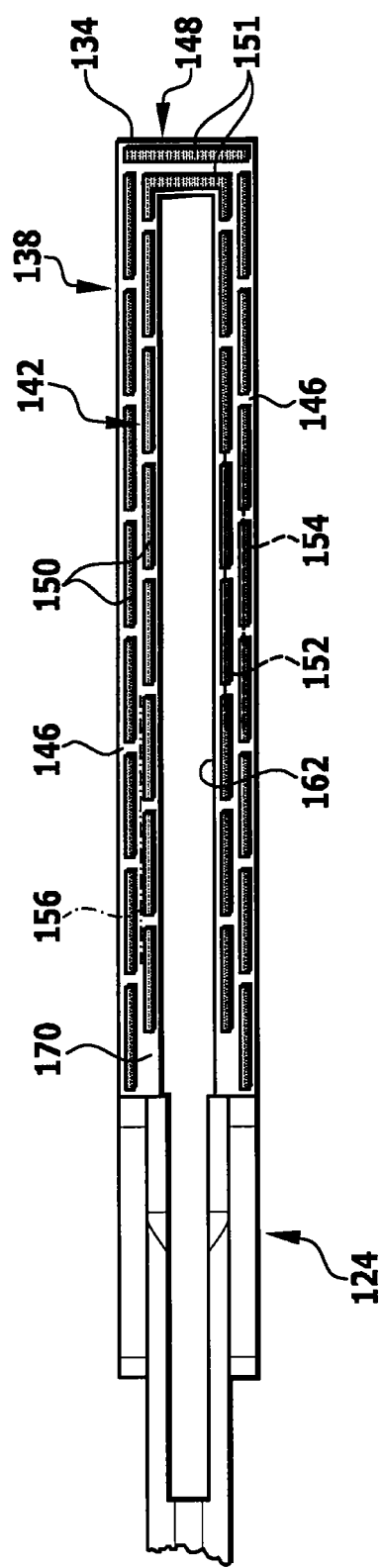
FIG. 7 shows a top view of a schematically shown tool element surface of the instrument from FIG. 6 in the direction of arrow B.

As an alternative or in addition, the surgical system 10 may comprise, instead of the instrument 12, also a surgical instrument, for example, in the form of an instrument 120 schematically shown in FIGS. 6 and 7. The instrument 120 comprises two branches 124 and 126 mounted on one another pivotable in relation to one another about a pivot axis 122. Finger rings 128, 130, which together define an actuating means 132 for actuating the instrument 120, are formed at a proximal end of the branches 124, 126.

Starting from free, distal ends 134 and 136 of the branches 124 and 126 are formed tool elements 138 and 140 pointing towards one another on the insides of same. The tool elements 138 and 140 have an identical design and lie opposite one another in a position of proximity of the ends 134 and 136 and have a minimal distance from one another in this position. Each tool element 138, 140 comprises an RF electrode 142, 144, which have an identical and essentially U-shaped design. Each RF electrode 142, 144 comprises two electrode sections 146, running parallel to one another and extending in a direction at right angles to the pivot axis 122, as well as an electrode section 148 running at right angles to same, adjacent to the ends 134, 136.

The structure of the RF electrodes 142, 144 is described in detail below, for example, in connection with FIG. 7 based on the RF electrode 142.

RF electrode 142 comprises a total of 30 electrode segments 150, whereby 15 electrode segments each are arranged offset to one another in two rows of electrodes 152, 154 parallel to one another along each electrode section 146 and electrically insulated from each other. The electrode segments 150 have a linear and strip-shaped design. They define between them an electrode center line 156, which likewise has a U-shaped design corresponding to the shape of the RF electrode 142. Two other electrode segments 151, which complete the rows of electrodes 152 or 154 of the electrode sections 146, respectively, are arranged in the area of the electrode section 148. Thus, the electrode segments 150 and 151 are arranged offset to one another in a direction defined by the electrode center line 156.

To be able to apply an RF current to the electrode segments 150, 151, these are each arranged in an electrically conductive manner with an RF terminal 158 in proximal end areas of the branches 124, 126 adjacent to the finger rings 128, 130. The RF terminals 158 can be connected to the RF current generator 18 with corresponding connecting lines or cables.

Because of the identical design of the RF electrodes 142 and 144, electrode segments 150 and 151 which are the same size or essentially the same size lie opposite one another and point towards one another in the position of proximity. They form a pair of electrode segments, which is designated as a whole with the reference number 168. Thus, the instrument 120 comprises a total of 32 pairs of electrode segments 168.

The tool elements 138 and 140 also define flat tool element surfaces 170, which have a U-shaped design. The electrode segments 150 and 151 do not protrude over the tool element surface 170.

The instrument 120, which has an overall tong-shaped design, may likewise be used for connecting tissues, whereby these are held gripped between the tool elements 138, 140 and then are welded or sealed to one another by means of corresponding application of current to the electrode segments 150, 151. As in connection with the function of the instrument 12 described, a current feed of the electrode segments 150 may be carried out sequentially for this, i.e., circulating in a U-shaped manner, after feeding an electrode segment 150 with current, the nearest electrode segment 150 of the adjacent row of electrodes 152, 154 is fed current until all electrode segments 150, 151 were fed current once. In this way, a two-row connecting line for connecting two tissues can be produced. As an alternative, a simultaneous current feed of two or even more electrode segments 150, 151 is also conceivable in the instrument 120, whereby electrode segments 150, 151, which are adjacent to one another, are preferably not fed current simultaneously, but rather preferably at least one, preferably two or three electrode segments 150, 151 remain currentless between electrode segments 150, 151 that are fed current simultaneously.

The instrument 120 may optionally also comprise a cutting means 160, as it is schematically shown in FIG. 6. A slot 162 each is formed between the electrode sections 146 at the tool elements 138, 140. A cutting element 164 with the cutting edge 166 pointing in the direction of the slot 162 of the branch 124 is held and can optionally be moved in relation to the tool element 136 in the slot 162 of the branch 126. Thus, for example, the tissue held between the tool elements 138 and 140 can be cut already when the branches 124 and 126 are closed. Optionally, the cutting element 164 may also be used in monopolar or bipolar mode, whereby, for example, the RF electrode 142 can be used as a counterelectrode to the cutting element 164 in bipolar mode. For the monopolar operation, an RF current is applied only to the cutting element 164 and a neutral electrode is then arranged as a counterelectrode at the body of the patient. In both cases, the cutting element 164 is preferably also connected in an electrically conductive manner to a contact of the RF terminals 158.

FIGS. 8 through 11 show a variant of the instrument 12 which is distinguished by the design of the second tool element which is designated with reference number 16' in FIGS. 8 through 11. Tool element 16' adopts a circular ring shape in an operating position, in which it can be brought into the position of proximity described above. It comprises two circular ring sections 180 and 182, which extend each over an angle of approx. 180° in relation to the longitudinal axis 54. Free ends of the circular ring sections 180, 182 are only half as wide as the circular ring sections 180, 182 in the remaining area and are used as bearing blocks 184 and 186. Bearing blocks 184 and 186 are each provided with a cross hole 188 and 190, into which a cylindrical rod 192 is inserted. Bearing blocks 184 lie against bearing blocks 186 on their side facing the longitudinal axis 54. The rod 192 is fixed adapted to rotate in unison in the cross holes 190 of the circular ring section 182. The cross hole 188 is dimensioned in its inside diameter such that the circular ring section 180 is pivotable in relation to the rod 192 about a pivot axis 242 defined by same and thus in relation to the circular ring section 182.

The two circular ring sections 180 and 182 are each additionally coupled via rod-shaped connecting rod 194 with a holding member 84', which defines a holding member longitudinal axis coinciding with the longitudinal axis 54. The holding member 84', similar to holding member 84, is coupled or can be coupled with the force transmission member 80, and in this way can be moved in relation to the shaft 24 in the distal and proximal direction. For the movable articulation of the connecting rod 194 at holding member 84', the latter is provided in the area of its distal end with a slot 204, which extends transversely to a longitudinal axis defined by the rod 192. In this way, two legs 206 are formed, which are provided with an aligning cross hole 208, into which a cylindrical mounting pin 210 is inserted adapted to rotate in unison. The connecting rods 194 are provided at their first ends with a mounting hole 212, through which the mounting pin 210 extends and which has an inside diameter to make possible a pivoting movement of connecting rods 194 about a pivot axis defined by the mounting pin 210.

Approximately on the proximal side of the slot 204, a longitudinal slot or slotted hole 214, which is passed through by the rod 192, extends in the holding member 84' further in the proximal direction. In this way, the rod 192 is defined and is displaceable parallel to itself in a direction parallel to the longitudinal axis 54. A proximal end of the slotted hole 214 forms a proximal end stop for the rod 192, a distal end 218 of the slotted hole 214 forms a distal end stop for the rod 192.

An actuating mechanism 222, which comprises a sleeve-like force transmission element 220, whose inside diameter is adapted to the outside diameter of holding member 84' and thus is displaceable on holding member 84' in the distal and proximal direction, is used to move the rod 192. The force transmission element 220 is, adjacent to its distal end 224, provided with a hole 226, which the rod 192 passes through. The rod 192 is rotatable in relation to the hole 226. The actuating mechanism 222 can further form a part of the actuating mechanism 76 described above. This means that a movement of the rod 192 is possible, for example, even by a pivoting of the actuating members 100 in relation to one another. As an alternative, it would be conceivable to provide another actuating means similar to actuating mechanism 76, which comprises one or two other actuating members, similar to the actuating members 100, to implement specifically a relative movement between the force transmission element 220 and the holding member 84'.

On the top sides of the circular ring sections 180 and 182 are arranged two bearing blocks 228 each, which are parallel to one another and which, parallel to the cross hole 208, are provided with holes 230. Between the bearing blocks 228, another free end of the connecting rod 194 each is pivotably mounted on the bearing shaft 200 inserted in the holes 230. Due to the described arrangement of the connecting rods 194, which may also be designated as articulating members, it is guaranteed that with one end at the second tool element 16', they act on a point of action or hinge point, which is spaced away from the pivot axis 242.

Figure 8:
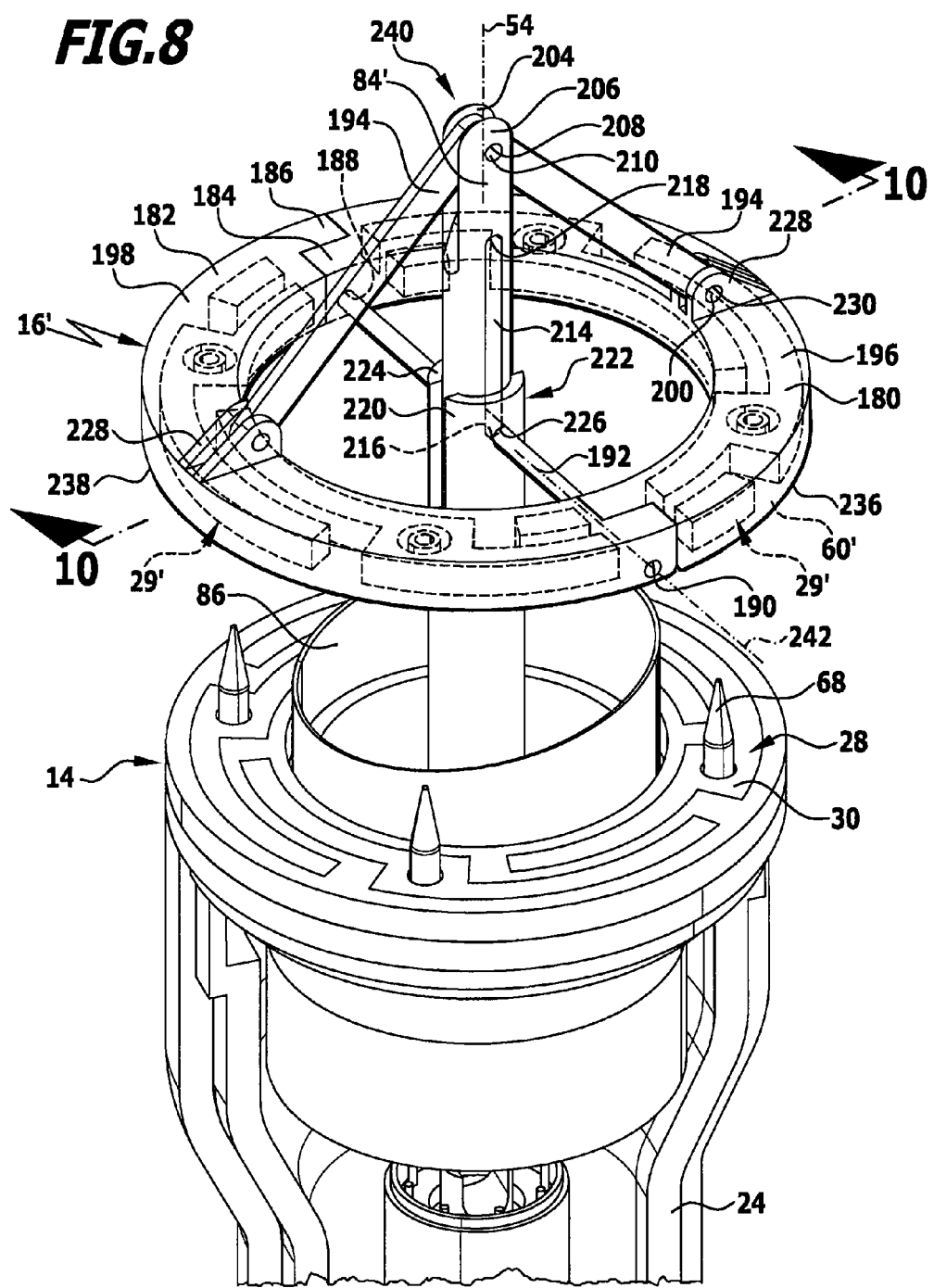
FIG. 8 shows a schematic view similar to FIG. 2 of an alternative embodiment of the instrument in a tissue gripping position.
Figure 9:
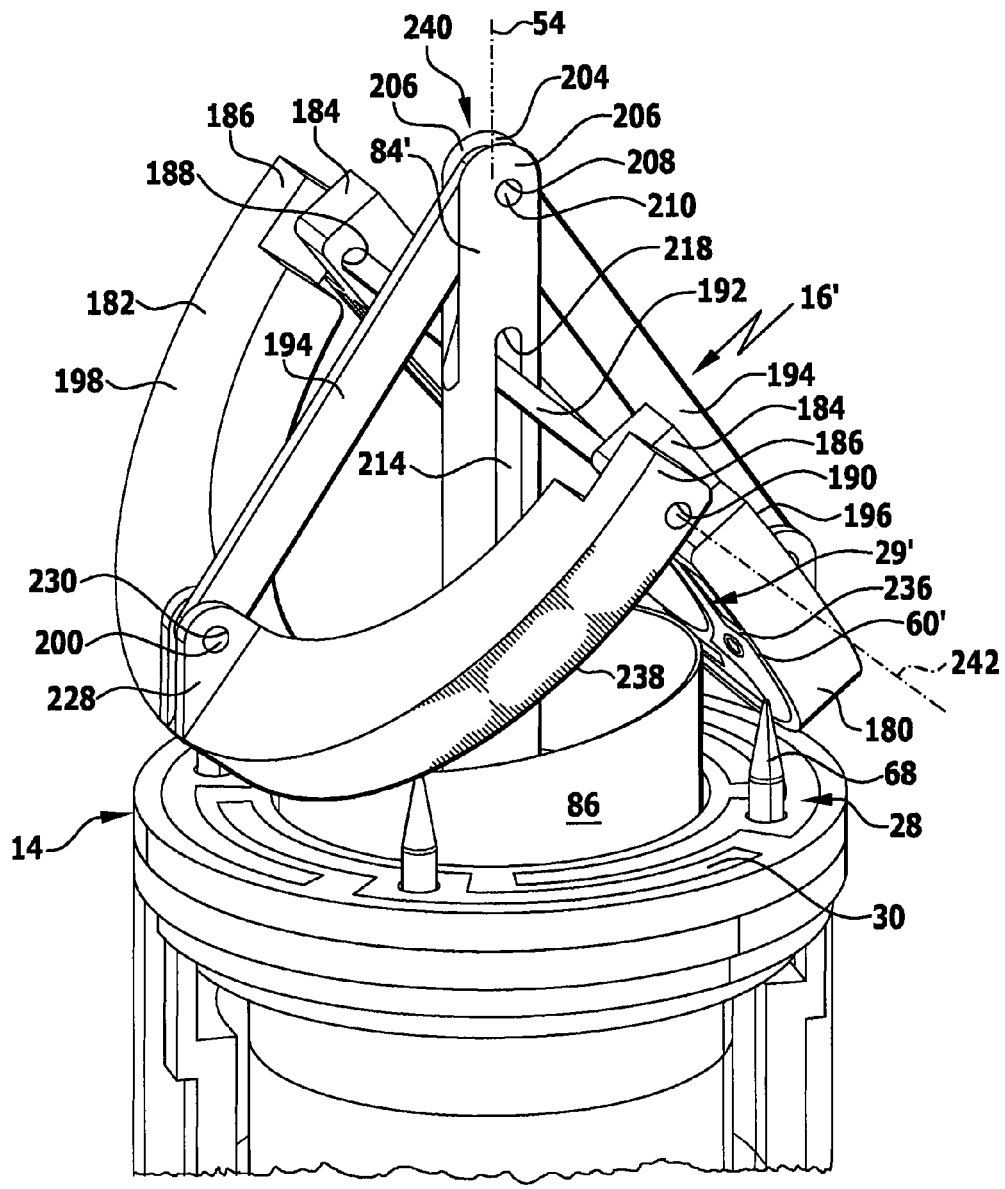
FIG. 9 shows a view corresponding to FIG. 8 of the instrument shown there with partly unfolded second tool element.
Figure 10:
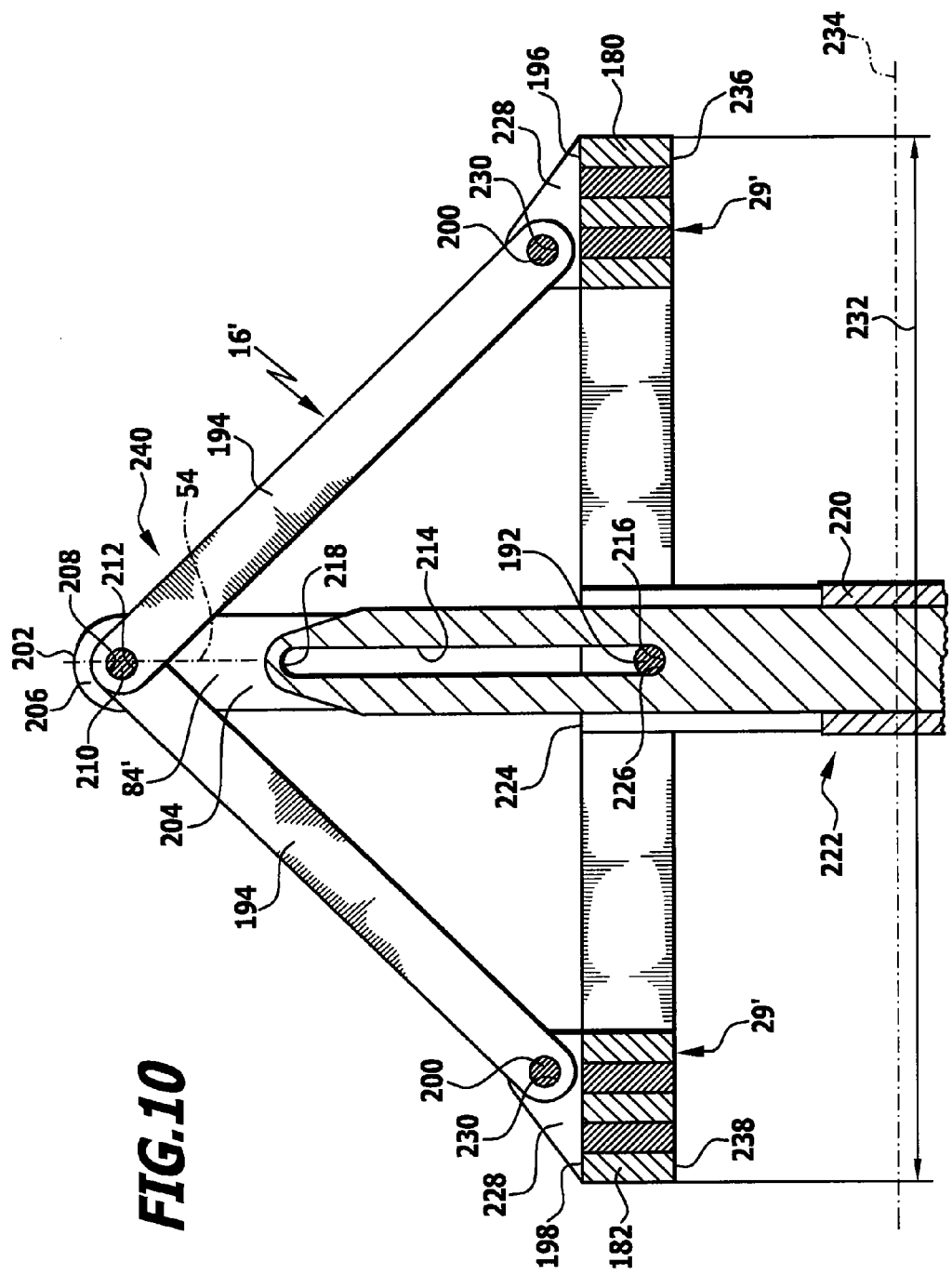
FIG. 10 shows a sectional view along line 10-10 in FIG. 8.
Figure 11:
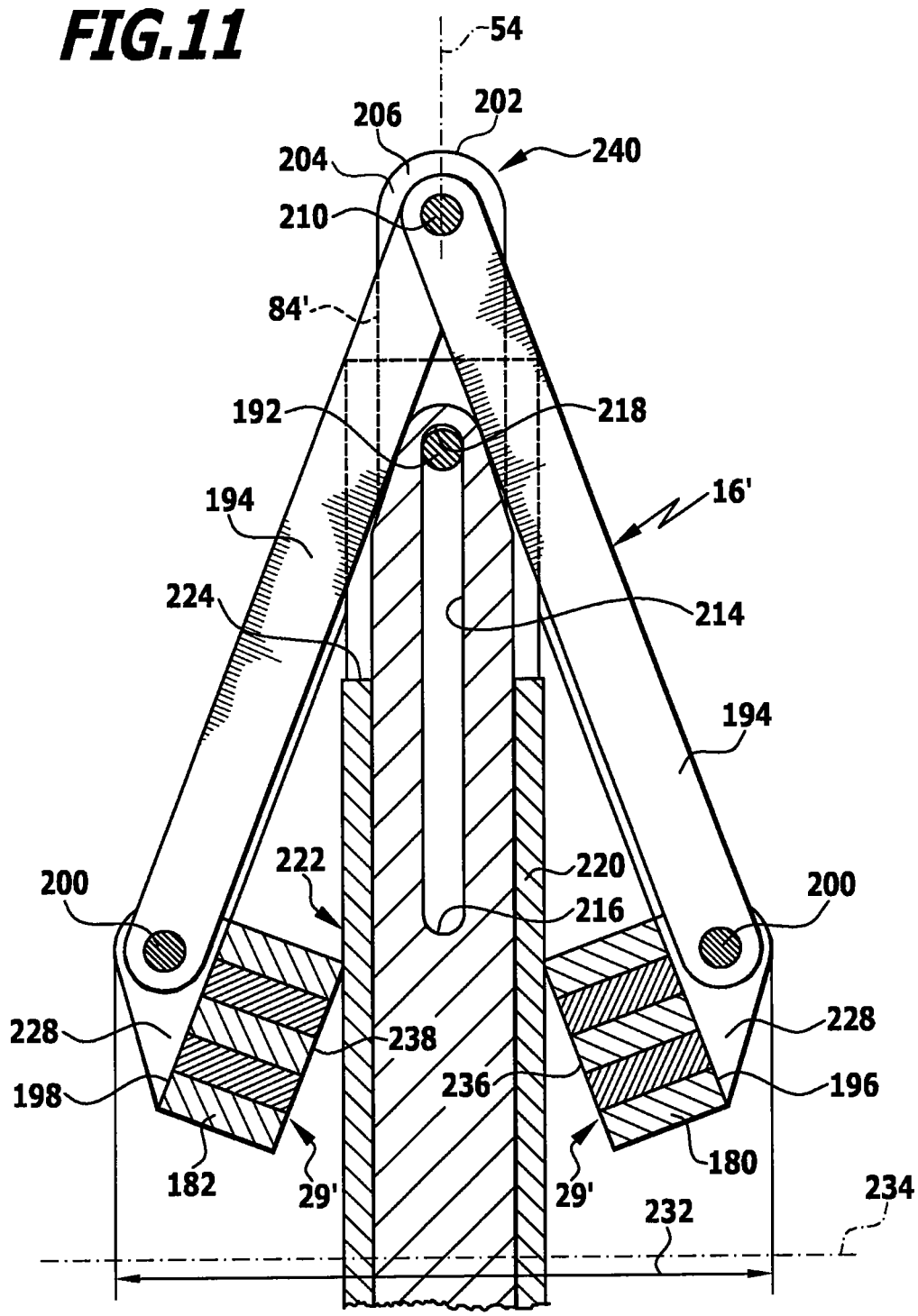
FIG. 11 shows a schematic sectional view similar to FIG. 10 of the second tool element folded up in a position as shown in FIG. 9.
Figure 12:
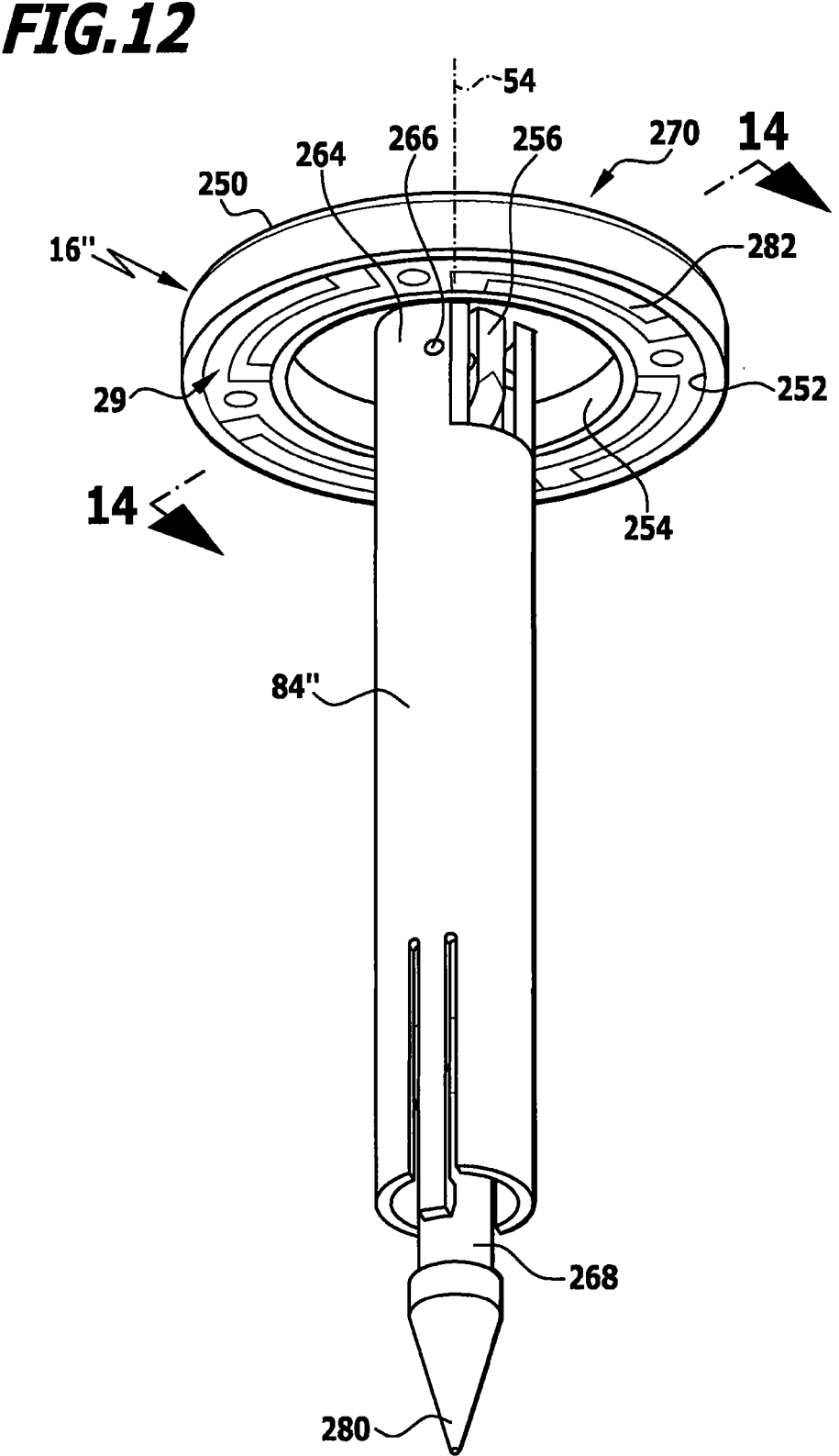
FIG. 12 shows a perspective schematic view of an alternative embodiment of a second tool element.
Figure 13:
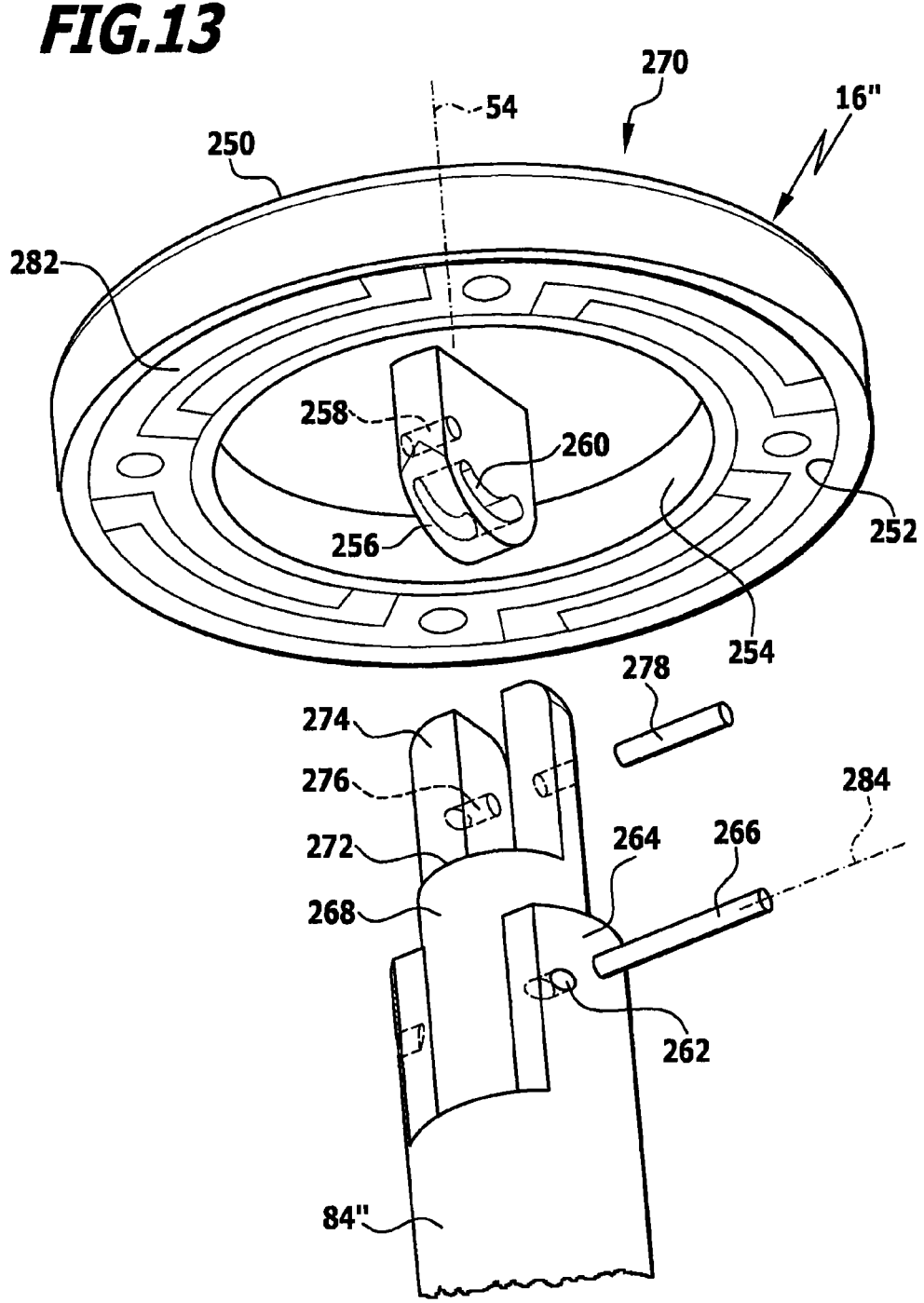
FIG. 13 shows an exploded view of a part of the second tool element shown in FIG. 12.

Using the actuating mechanism 222, the second tool element 16' can be brought from the operating position already mentioned, which is schematically shown in FIGS. 8 and 10, into the removal position, which is shown, for example, in FIG. 11. FIG. 9 schematically shows an intermediate position, i.e., a position between the operating position and the removal position. As can be easily seen by a comparison of the two FIGS. 10 and 11, a surface area of a vertical projection of the second tool element 16' is on a projection plane 234, which runs at right angles to the longitudinal axis 54, i.e., to the shaft direction in the area of second tool element 16', is smaller in the removal position than in the operating position. This is achieved by a movement of the sleeve-like force transmission element 220 starting from the operating position, in which the rod 192 stops at the proximal end 216 and bottom sides 236 and 238 of the circular ring sections 180 and 182 extend parallel to the projection plane 234. If the force transmission element 220 is moved in the distal direction, the rod 192 is forcibly guided in the slotted hole 214 in the distal direction. Due to the articulated connection of the circular ring sections 180 and 182 in relation to one another and via the two connecting rods 194 with the holding member 84', the circular ring sections 180 and 182 pivot about the pivot axis 242 in the direction of the longitudinal axis 54. The second tool element 16' is in this way folded together or folded up. Thus, due to the articulated arrangement of the circular ring sections 180 and 182 by means of the connecting rods 194, a folding mechanism 240 is formed for transferring the second tool element 16' from the operating position into the removal position.

The design of the bottom sides 236 and 238 of the second tool element has not been mentioned up to now. This may have either a single, essentially continuous ring electrode, which forms a single counterelectrode to RF electrode 28 of the first tool element 14. As an alternative, an RF electrode with two or more electrode segments 31, preferably corresponding to RF electrode 29, may also be formed on the bottom sides 236 and 238 similar to RF electrode 29. This then makes possible a connecting of tissues 116 in the operating position in the manner described above.

After connecting the tissues, the folding mechanism 240 can then be actuated, for example, by the corresponding actuating of the described actuating mechanism 222, as a result of which the holding member 84' is moved in the distal direction. If the force transmission element 220 is, for example, arranged fixed in relation to the shaft 24, then the second tool element 16' can be automatically folded up by a movement in the distal direction of the force transmission member 80. Due to the markedly reduced area requirement in the removal position, the second tool element can be guided through a connecting site formed by the connecting of the tissues 116 during the removal of the instrument 12, and without expanding the connecting site, which is markedly more sparing then guiding the second tool element through the connecting site in the operating position.

It goes without saying that electrically conductive connections of electrode 29 to the RF terminal contacts 50 can be routed, for example, via the connecting rods 94 and the holding member 84' to the RF terminal contacts 50 in the proximal end area of the shaft 24.

Another variant of a second tool element is designated as a whole with the reference number 16" in FIGS. 12 through 15. It replaces, for example, the above-described tool elements 16 and 16' of the instrument 12.

The second tool element 16" has an essentially plate-like design with a slightly convex, curved outside 250 pointing in the distal direction.

A ring groove 252, which is open pointing in the proximal direction, is formed on the bottom side of the second tool element 16". In the center is formed an essentially circular recess 252, in which an essentially cuboid bearing projection is arranged, which is designed as projecting coaxially to the longitudinal axis 54 in the proximal direction from the bottom side of second tool element 16". The bearing projection 256 is provided with a cross hole 258, which runs skew in relation to longitudinal axis 54. Furthermore, a curved guide slot 260, which is curved convexly pointing in the proximal direction, is formed at the bearing projection 256. A proximal end of the bearing projection 256 has a rounded outer contour.

The second tool element 16" is pivotably mounted on a sleeve-like holding member 84". For this purpose, the holding member 84" is provided with a cross hole 262, which passes through a wall 264 of the holding member 84" at two sites. A mounting pin 266 adapted to rotate in unison is inserted into the cross hole 262. It simultaneously passes through the cross hole 258 such that the bearing projection 256 is pivotable about a pivot axis 284 defined by the mounting pin 266. To be able to actuate a folding mechanism 270 provided also with the second tool element 16", a force transmission element 268 is provided, which has an essentially rod-shaped design and the holding member 84" passes through coaxially to the longitudinal axis 54. From an end surface 272 on the distal side of the force transmission element 268, two bearing journals 274 are arranged parallel to one another and projecting pointing in the distal direction, which are each passed through by an aligning hole 276. Another mounting pin 278, which is oriented parallel to the mounting pin 266, is inserted adapted to rotate in unison into the holes 276. An outside diameter of the mounting pin 278 is dimensioned such that it can pass through the guide slot 260 and can be moved in relation to same.

A proximal end 280 of the force transmission element 268 can preferably be coupled with the force transmission member 80, such that the second tool element 16" can also be moved as a result of a movement of same.

A circular electrode element 282, which preferably comprises an RF electrode 29 in the manner as described above, which is not shown in detail in FIGS. 12 through 15 for the sake of clarity, is inserted into the ring groove 252. As an alternative, a simple, continuous ring electrode may also be formed at the electrode element 282.

Figure 14:
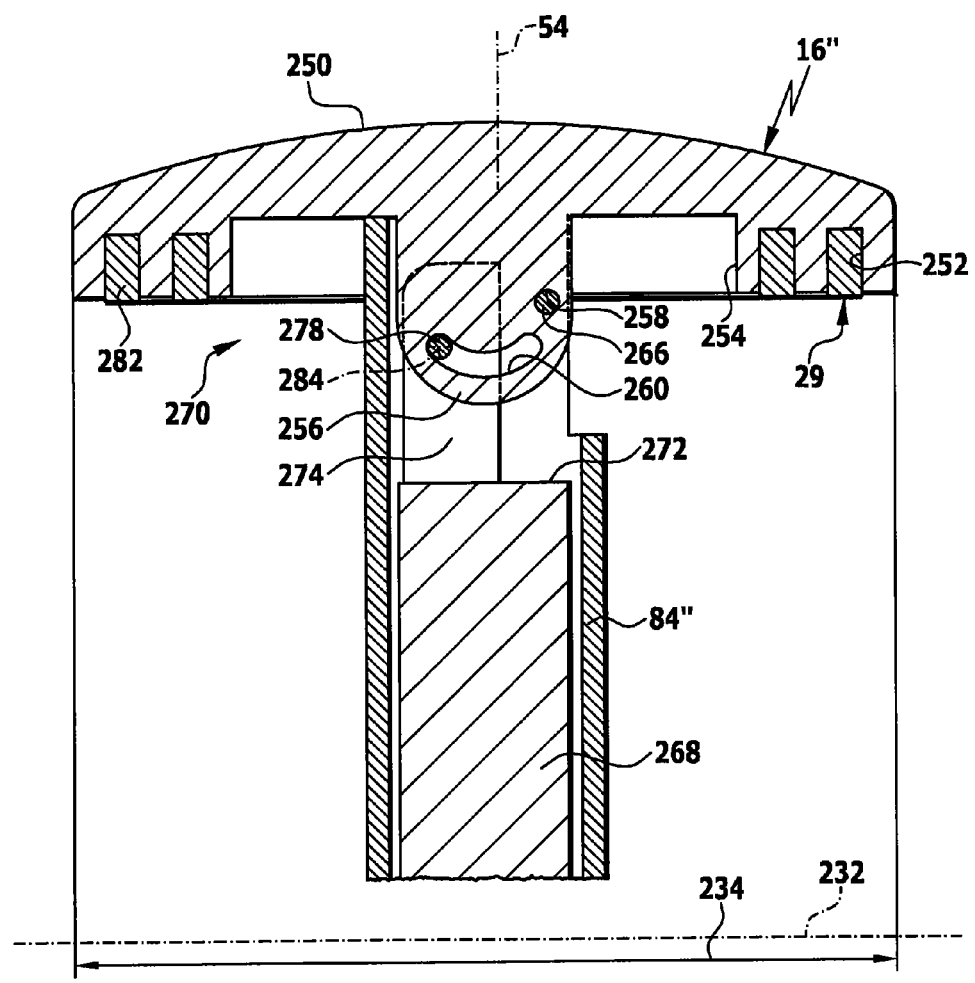
FIG. 14 shows a sectional view along line 14-14 in FIG. 12.
Figure 15:
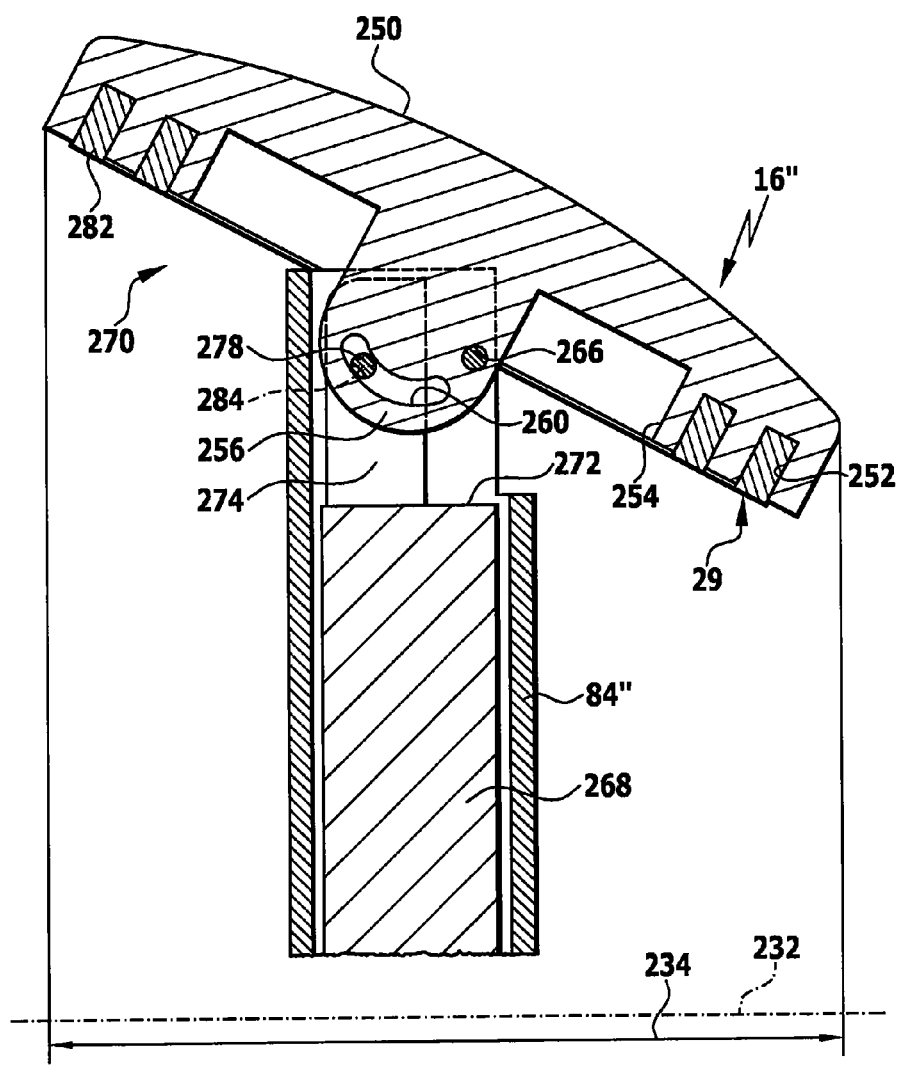
FIG. 15 shows a schematic sectional view similar to FIG. 14 of the exemplary embodiment shown there with partly unfolded second tool element.
Figure 16:
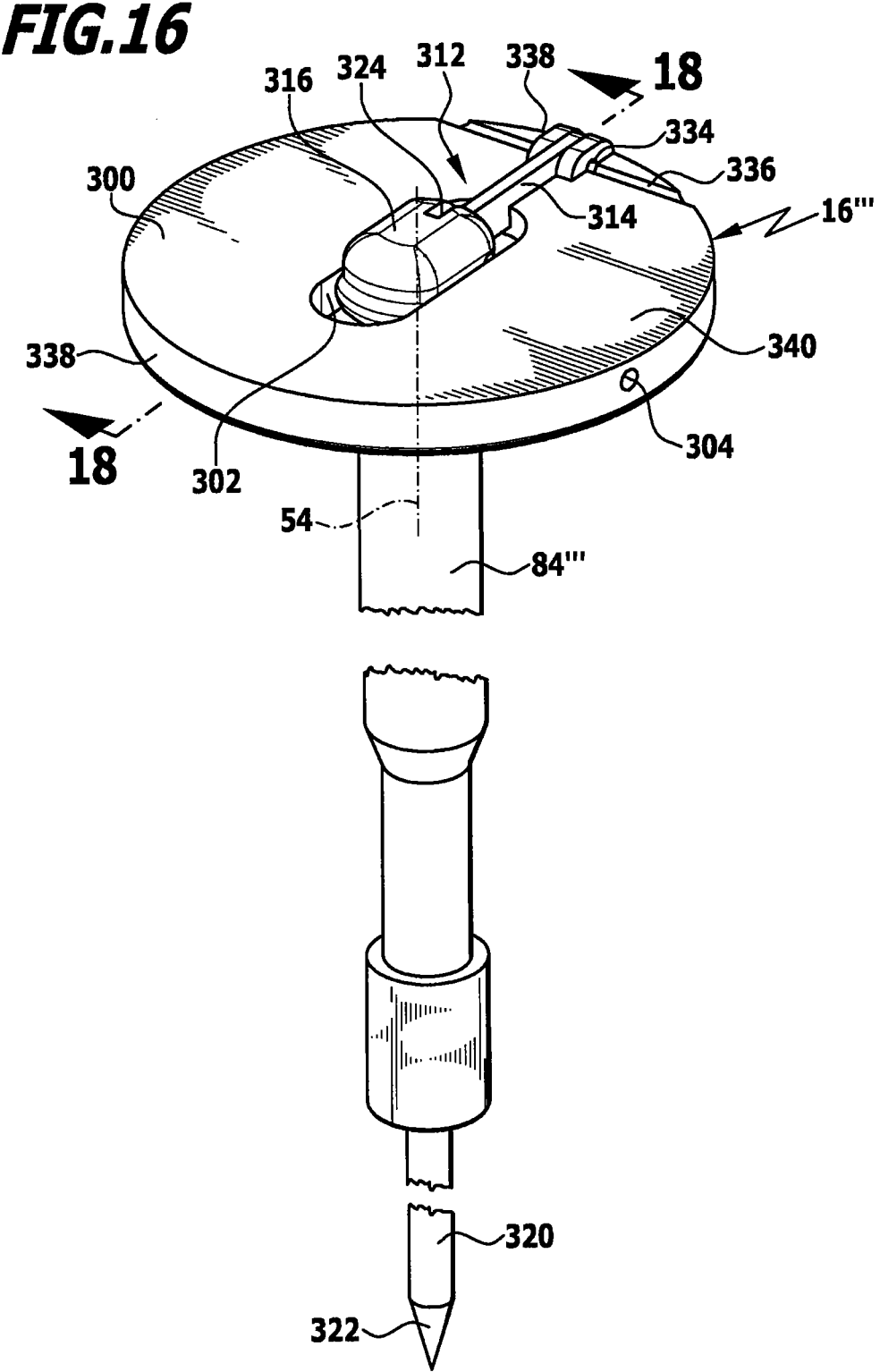
FIG. 16 shows a perspective schematic view similar to FIG. 12 of another exemplary embodiment of a second tool element.
Figure 17:
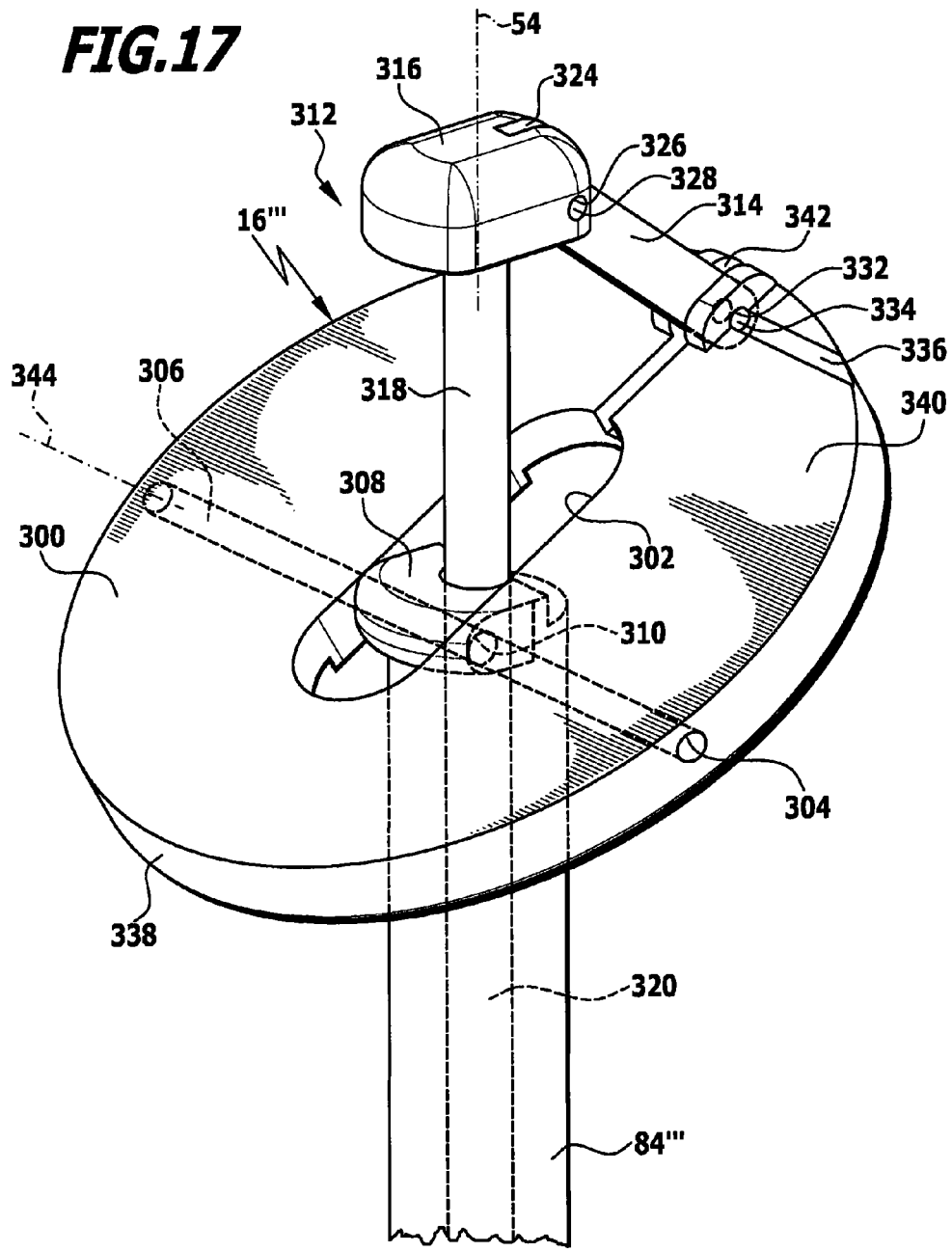
FIG. 17 shows an enlarged view of the second tool element from FIG. 16 in a partly sloped position.
Figure 18:
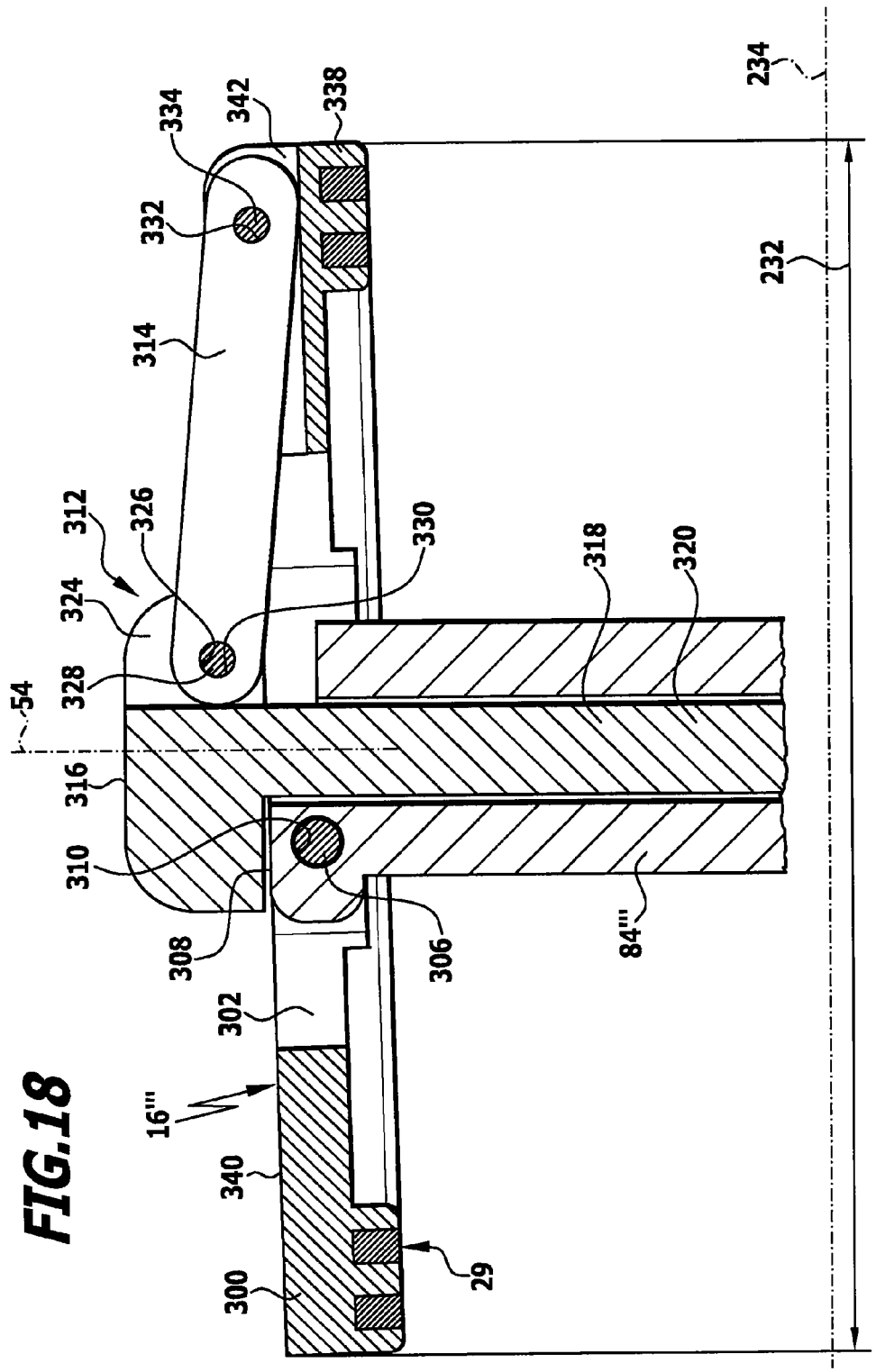
FIG. 18 shows a sectional view along line 18-18 in FIG. 16.
Figure 19:
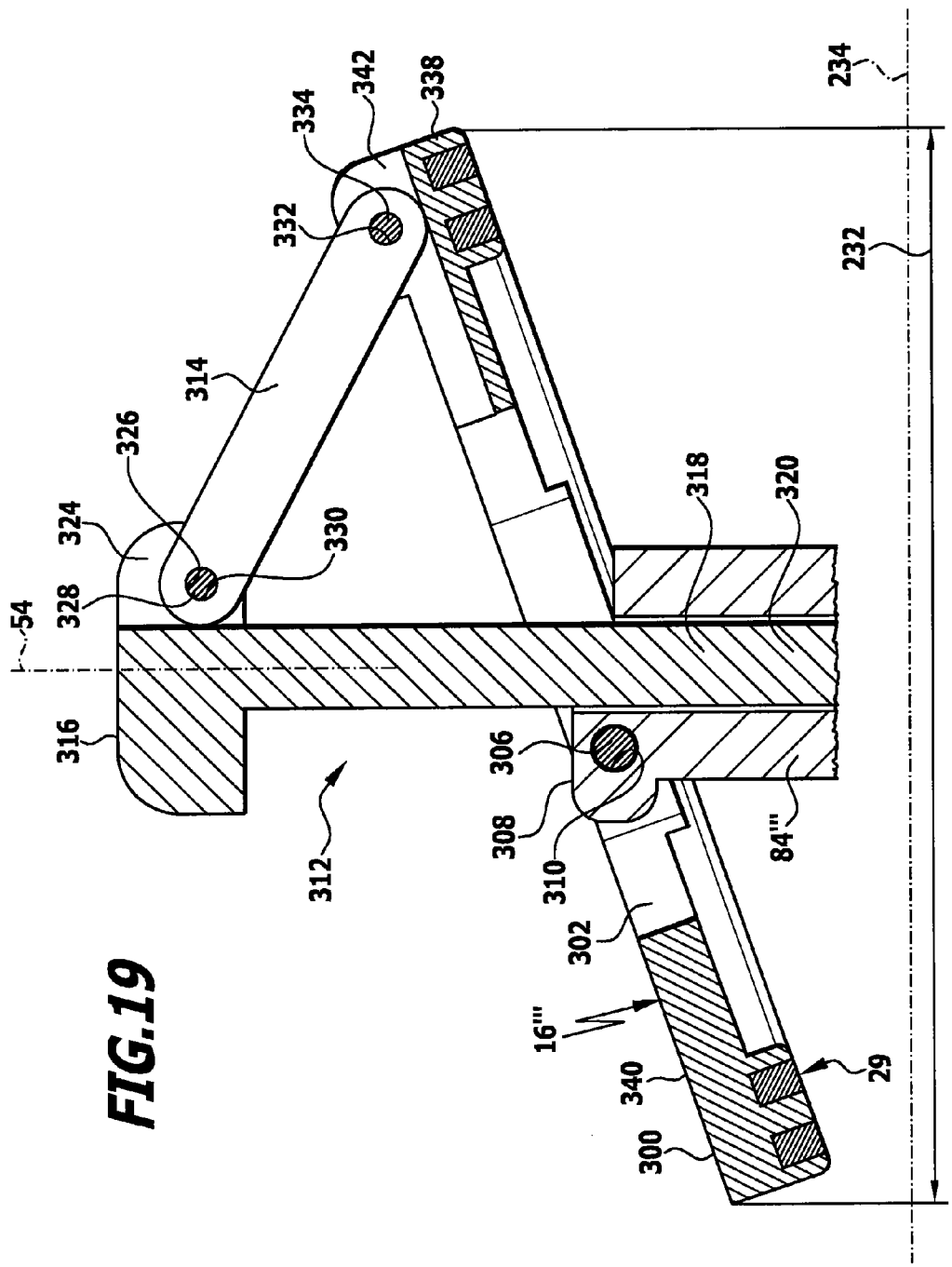
FIG. 19 shows a view similar to FIG. 18 with partly sloped second tool element in a position, as it is shown in FIG. 17.

For transferring the second tool element 16" from the operating position into the removal position, the force transmission element 268 is moved in the distal direction. Because of the specially curved guide slot 260, the mounting pin 278 is forcibly guided in same and thus brings about a forcibly guided pivoting of the second tool element 16" about the pivot axis 284. Essentially, the second tool element 16" can be pivoted about almost 90°, such that in this variant of the tool element 16" as well, a vertical projection 232 of same onto the projection plane 234 in the removal position is smaller than in the operating position, as this is schematically shown in FIGS. 14 and 15. In this way, an overexpansion of the connecting site between the tissues 116 connected to one another is prevented in the removal position when removing the instrument 12.

Another embodiment of a second tool element, which is provided as a whole with the reference number 16''', is shown in FIGS. 16 through 19. It can be used in the instrument 12 instead of the previously described second tool elements 16, 16' and 16".

The second tool element 16''' has an essentially plate-like design and comprises a disk 300. Disk 300 is provided in its center with a transversely running, oblong, oval slot 302. A hole 304 passes through the disk 300 somewhat laterally offset to its center, which lies in the area of the slot 302. A mounting pin 306, which likewise passes through the slot 302, is inserted adapted to rotate in unison into the hole 304. A distal end of a holding member 84''', which has a sleeve-like design, protrudes into the area of the slot 302. On the side proximally from its end 308, the holding member 84''' is provided with a hole 310, whose inside diameter is adapted to the outside diameter of the mounting pin 306 so that the mounting pin 306 is rotatable in same in relation to the hole 310. All in all, this then makes possible a pivoting of the disk 300 about a longitudinal axis defined by the mounting pin 306.

A folding mechanism 312, which couples the disk 300 via a connecting rod 314 in an articulated manner with a distal end 316 of a force transmission element 318, is used for the forcibly actuated pivoting of the disk 300. The force transmission element 318 has an extended, rod-shaped section 320, whose proximal end 322 can be coupled with the force transmission member 80. The end 316 is thickened in a head-shaped manner against the section 320 and shaped almost cuboid. On one side of same is formed a lateral open slot 324. Further, a cross hole 326 is provided, which passes through the slot 323 transversely. A mounting pin 328 is inserted adapted to rotate in unison into the cross hole 326. The rod-shaped connecting rod 314 is likewise provided with a hole 330 and is mounted pivotably on the mounting pin 328. Adjacent to an opposite end of the connecting rod 314 is provided another hole 332. It is used for mounting the connecting rod 314 on another mounting pin 334. This is inserted into another hole 336 of the disk 300. The hole 336 is oriented parallel to the hole 304 and arranged outside the slot 302 adjacent to an edge 338 of the disk 300, and lying opposite the hole 304 in relation to the longitudinal axis 54. Starting from the edge 338, a groove 342, into which the end of the connection rod 314 with its hole 332 dips, is provided on a top side 340 of the disk 300. In this way, the connecting rod 314 is mounted in an articulated manner on the mounting pin 334. Thus, the connecting rod 314 with an end at the second tool element 16''' acts on a point of action or hinge point, which is spaced away from the pivot axis 344 defined by the longitudinal axis of the mounting pin 306.

The folding mechanism 312 is actuated by the force transmission element 318 being moved in the distal direction. The result of this is that the connecting rod 314 is bent in relation to the disk 300. The further the force transmission member 318 is moved in the distal direction, the further the connecting rod 314 draws the area of the disk 300 in the distal direction, at which the groove 342 is provided. In an extreme position, the disk 300 is then aligned almost parallel to the longitudinal axis 54. All in all, it is thus also possible in the second tool element 16''' to embody a removal position, in which a vertical projection 232 of same onto the projection plane 234, which runs at right angles to the longitudinal axis 54, is smaller than in the operating position.

An RF electrode 29 may likewise be arranged or formed at the second tool element 16''' in a form as described above in the second tool element 16. As an alternative, it is also conceivable to provide a self-contained, circular electrode, which is not divided into electrode segments. Similar to how the second tool element 16'' comprises the electrode element 282, electrode elements may likewise be provided in second tool elements 16' and 16''', for example, in the form of the electrode element 282 or else even the electrode element 52.

As already mentioned above in connection with the second tool element 16', the RF electrodes provided at the second tool elements 16'' and 16''' may usually be connected to the RF terminal contacts 50 by providing corresponding electrically conductive connections at the instrument 12.

All above-described first and second tool elements 14, 16, 16', 16'', 16''', as well as 138 and 140 are preferably composed of either electrically conductive or electrically insulating components. Also conceivable are components, which are partly electrically conductive or partly electrically insulating. The components themselves may especially be produced completely from electrically conductive or electrically insulating materials, whereby the electrically insulating components may also be produced from an electrically conductive material, which is especially provided with an electrically insulating outer shell or coating. Especially plastics, which still have sufficient strength at the temperatures occurring during the use of the surgical system 10, may be used as electrically insulating or nonconducting materials. For example, both thermoplasts and duroplasts are suitable. As an alternative, ceramic material may also be used as insulating material. The components of the tool elements 14, 16, 16', 16'', 16''', as well as 138 and 140 may especially be made of a ceramic. A ceramic to be used has especially the advantage over many plastics that it also has a sufficient stability at very high temperatures. The RF electrodes 28 and 29 are preferably made of a metal or a metal alloy. As an alternative, the use of electrically conductive ceramics is also conceivable for forming the RF electrodes 28 and 29, provided that they meet the requirements of the application of RF current.

The tool elements 14, 16, 16', 16'', 16''', as well as 138 and 140 may, for example, be produced as described below. The individual parts, units or components of the tool elements 14, 16, 16', 16'', 16''', as well as 138 and 140 may especially be produced separately and then be joined together, for example, by bonding. As an alternative, it is, for example, also possible to insert the electrically conductive parts of the RF electrodes 28 and 29 as inserts into a plastics injection molding die and to injection-mold with a plastic. As already mentioned, the electrodes may be made from a metal or an electrically conductive ceramic. In a segmenting of the RF electrodes 28 and 29 as described above, a corresponding number of electrically conductive electrode segments made of a metal or a metal alloy or an electrically conductive ceramic must, for example, then be inserted into the plastics injection molding die before injection molding with a suitable plastic.

In a purely ceramic design of the tool elements 14, 16, 16', 16'', 16''', as well as 138 and 140, a ceramic powder injection molding process is offered, e.g., the so-called "2K CIM" technology, a two-component micro-ceramic powder injection molding process. Here, two different ceramics are injected in an injection molding process, which form the electrically conductive and electrically insulating parts in the finished tool elements 14, 16, 16', 16'', 16''', as well as 138 and 140. After the injection molding, two different ceramics are sintered together. They may be, for example, an $Al_2O_3$ ceramic and a mixed ceramic made of $Al_2O_3$ and TiN.

The invention claimed is:

1. A surgical instrument for connecting body tissue with a connecting means for connecting body tissue, the connecting means comprising two tool elements movable in relation to one another, the instrument comprising a cutting means with a cutting element for cutting tissue, the cutting element being movable in relation to at least one of the tool elements,
    the cutting means being designed as an RF cutting means that has the cutting element and a counterelectrode lying opposite same, to which RF current can be fed;
    the counterelectrode is formed on one of the tool elements; and
    the cutting element has a cutting edge that defines a cutting plane which is sloped in relation to a tool element surface, on which the counterelectrode is formed, wherein:
    the cutting edge of the cutting element and the counterelectrode have a circular design.

2. A surgical instrument in accordance with claim 1, wherein the cutting means is designed in the form a monopolar cutting means.

3. A surgical instrument in accordance with claim 1, wherein the cutting means is designed in the form of a bipolar cutting means.

4. A surgical instrument in accordance with claim 1, wherein the cutting edge has a self-contained circular design.

5. A surgical instrument in accordance with claim 1, wherein the instrument has at least one cutting terminal connected in an electrically conductive manner to the cutting means.

6. A surgical instrument in accordance with claim 5, wherein the at least one cutting terminal is connected in an electrically conductive manner to the cutting element.

7. A surgical instrument in accordance with claim 1, wherein the tool elements are designed as pivotable and/or displaceable in relation to one another.

8. A surgical instrument in accordance with claim 1, wherein the cutting element can be rotated in relation to the counterelectrode about a longitudinal axis defined by the instrument in the area of the connecting means.

9. A surgical instrument for connecting body tissue with a connecting means for connecting body tissue, the connecting means comprising two tool elements movable in relation to one another, the instrument comprising a cutting means with a cutting element for cutting tissue, the cutting element being movable in relation to at least one of the tool elements,
    the cutting means being configured in the form of an RF cutting means that has the cutting element and a counterelectrode wherein the counterelectrode is arranged to lie opposite to the cutting element and wherein the cutting element and the counterelectrode are feedable with RF current;
    the counterelectrode has a circular design and is formed on one of the tool elements; and the cutting element has a cutting edge, formed to a circular shape and thereby defining a cutting plane, which is sloped in relation to a tool element surface, on which the counterelectrode is formed, so that a defined cutting spark is producible in an area in which a distance between the cutting element and the counterelectrode is minimal, such that the tissue is simultaneously coagulated during the cutting and stops bleeding directly during the cutting.

10. A surgical instrument in accordance with claim 9, wherein the cutting means is designed in the form a monopolar cutting means.

11. A surgical instrument in accordance with claim 9, wherein the cutting means is designed in the form of a bipolar cutting means.

12. A surgical instrument in accordance with claim 9, wherein the cutting edge has a self-contained circular design.

13. A surgical instrument in accordance with claim 9, wherein the instrument has at least one cutting terminal connected in an electrically conductive manner to the cutting means.

14. A surgical instrument in accordance with claim 13, wherein the at least one cutting terminal is connected in an electrically conductive manner to the cutting element.

15. A surgical instrument in accordance with claim 9, wherein the tool elements are designed as pivotable and/or displaceable in relation to one another.

16. A surgical instrument in accordance with claim 9, wherein the instrument comprises an actuation means for moving the tool elements in relation to one another.

17. A surgical instrument in accordance with claim 9, wherein the instrument comprises a cutting actuation means for moving the cutting element and at least one of the tool elements in relation to one another.

18. A surgical instrument in accordance with claim 17, wherein the actuation means and/or the cutting actuation means are arranged or formed at a proximal end of the instrument.

19. A surgical instrument in accordance with claim 17, wherein the actuation means and/or the cutting actuation means comprise two actuation members pivotable in relation to one another, which are in operative connection with at least one of the tool elements or the cutting element for transmitting an actuation force for moving the at least one tool element in relation to the other tool element or the at least one tool element in relation to the cutting element.

20. A surgical system with a surgical instrument in accordance with claim 9 and at least one RF current generator, which can be selectively connected in an electrically conductive manner to the RF electrodes and/or the cutting element.

* * * * *